(12) United States Patent
Shing et al.

(10) Patent No.: US 10,759,729 B2
(45) Date of Patent: Sep. 1, 2020

(54) COMPOUNDS FOR TREATING DIABETES

(71) Applicant: The Chinese University of Hong Kong, Sha Tin, N.T., Hong Kong (CN)

(72) Inventors: Tony Kung Ming Shing, Hong Kong (CN); Wai-Lung Ng, Hong Kong (CN); Ho Chuen Li, Hong Kong (CN); Kit-Man Lau, Hong Kong (CN); Clara Bik San Lau, Hong Kong (CN)

(73) Assignee: The Chinese University of Hong Kong, Shatin, NT, Hong Kong (CN)

( * ) Notice: Subject to any disclaimer, the term of this patent is extended or adjusted under 35 U.S.C. 154(b) by 0 days.

(21) Appl. No.: 15/345,252

(22) Filed: Nov. 7, 2016

(65) Prior Publication Data
US 2018/0127343 A1    May 10, 2018

(51) Int. Cl.
*C07C 43/23*    (2006.01)
*C07C 41/30*    (2006.01)

(52) U.S. Cl.
CPC .............. *C07C 43/23* (2013.01); *C07C 41/30* (2013.01); *C07C 2601/14* (2017.05); *C07C 2601/16* (2017.05)

(58) Field of Classification Search
CPC ..... C07C 43/23; C07C 41/30; C07C 2101/14; C07C 2101/16
See application file for complete search history.

(56) References Cited

U.S. PATENT DOCUMENTS

2009/0156516 A1*  6/2009  Chen .................. C07H 7/04
                                                        514/35

OTHER PUBLICATIONS

Cobo et al. (Organic Letters, 2012, v. 14, No. 7, p. 1728-1731).*
Xu et al. (J. Mol. Recognit. 2015; 28: 467-479, published Mar. 5, 2015).*
Li ("Synthetic Studies towards Carbocyclic Analogues of Dapagliflozin", Thesis, The Chinese University of Hong Kong, Feb. 2016).*
Shing et al. (Angew. Chem. Int. Ed. 2013, 52, 8401-8405).*
Brown ("Bioisosteres in Medicinal Chemistry", Editor: Dr. Nathan Brown, Aug. 3, 2012, pp. 1-29 provided).*
Arjona, et al. "Synthesis and conformational and biological aspects of carbasugars." Chemical reviews 107, No. 5 (2007): 1919-2036.
Chao, et al. "SGLT2 inhibition—a novel strategy for diabetes treatment." Nature reviews drug discovery 9, No. 7 (2010): 551-559.
DeFronzo, et al. "Renal, metabolic and cardiovascular considerations of SGLT2 inhibition." Nature Reviews Nephrology 13, No. 1 (2017): 11-26.
Li, et al. "Regioselective and Stereospecific Cross-Coupling of Primary Allylic Amines with Boronic Acids and Boronates through Palladium-Catalyzed C☐ N Bond Cleavage." Angewandte Chemie International Edition 51, No. 12 (2012): 2968-2971.
Li, et al. "Pd-Catalyzed Regioselective and Stereospecific Suzuki-Miyaura Coupling of Allylic Carbonates with Arylboronic Acids." Organic letters 14, No. 1 (2011): 390-393.
Mascitti, et al. "On the importance of synthetic organic chemistry in drug discovery: reflections on the discovery of antidiabetic agent ertugliflozin." MedChemComm 4, No. 1 (2013): 101-111.
Ng, et al. "Palladium-Catalyzed Arylation of Carbasugars Enables the Discovery of Potent and Selective SGLT2 Inhibitors." Angewandte Chemie 128, No. 44 (2016): 14022-14025.
Ohtake, et al. "5a-Carba-β-d-glucopyranose derivatives as novel sodium-dependent glucose cotransporter 2 (SGLT2) inhibitors for the treatment of type 2 diabetes." Bioorganic & medicinal chemistry 19, No. 18 (2011): 5334-5341.
Shing, et al. "Design, Syntheses, and SAR Studies of Carbocyclic Analogues of Sergliflozin as Potent Sodium-Dependent Glucose Cotransporter 2 Inhibitors." Angewandte Chemie 125, No. 32 (2013): 8559-8563.
Sidera, et al. "Rhodium-catalysed asymmetric allylic arylation of racemic halides with arylboronic acids." Nature chemistry 7, No. 11 (2015): 935-939.

* cited by examiner

*Primary Examiner* — Robert H Havlin
(74) *Attorney, Agent, or Firm* — Kilpatrick Townsend & Stockton LLP

(57) ABSTRACT

The present invention provides a class of novel aryl pseudo-C-glycoside compounds that are effective for treating diabetes. Also provided are methods for making such compounds and methods for treating diabetes by administering such compounds to patients who have been diagnosed with diabetes or are at risk of developing diabetes.

8 Claims, 3 Drawing Sheets

COMPOUNDS FOR TREATING DIABETES

BACKGROUND OF THE INVENTION

Diabetes mellitus, often referred to simply as diabetes, encompasses a variety of conditions that involve disordered metabolism, the typical feature of which is abnormally high blood sugar levels (hyperglycemia). Blood sugar levels are controlled by a complex network of chemicals and hormones in the human body, including the hormone, insulin, produced by the beta cells of the pancreas. The abnormally high level of blood sugar seen in a diabetic patient is caused by defects in either insulin secretion or insulin action, attributable to a combination of hereditary, acquired, and environmental factors. Majority of diabetes are either type 1 diabetes, previously known as childhood-onset diabetes and insulin-dependent diabetes, or type 2 diabetes, previously known as adult-onset diabetes and insulin-independent diabetes.

Type 1 diabetes is characterized by loss of the insulin-producing beta cells of the islets of Langerhans in the pancreas, resulting in a deficiency of insulin production. The principal treatment for this type of diabetes is therefore delivery of artificial insulin, usually via injection. Type 2 diabetes is more common than type 1 diabetes with over 90% of affected people having type 2 diabetes. The latter is closely associated with modernization characterized by obesity and insulin resistance (reduced insulin sensitivity) although diminished insulin production is needed for development of overt hyperglycemia. Both twin and family studies support a strong genetic component for type 2 diabetes. Recent genetic implicate multiple common genetic variants in the development of type 2 diabetes although these factors only explained a small percentage of the variance of the genetic risk of type 2 diabetes.

Various factors are known to be indicative of a person's risk to develop type 2 diabetes, most of them strongly influenced by the person's lifestyle, age, ethnic background, and family history. The presence of at least one, often more, of these risk factors, such as a body mass index (BMI) in the range of obesity (especially central obesity due to accumulation of excess visceral fat as indicated by large waist circumference), elevated blood glucose or insulin level (especially elevated fasting or post prandial blood glucose or insulin level), and reduced sensitivity to insulin, predisposes a person to the high likelihood of developing type 2 diabetes, if no corrective measure is taken.

As people's living standards continue to improve globally, the number of individuals suffering from diabetes is also rapidly increasing. The World Health Organization (WHO) estimates that by 2030 the number of people living with diabetes will exceed 350 million worldwide. At the present time, an estimated 35% of all US adults and 50% of those aged 60 years or older have metabolic syndrome, a cluster of pre-diabetic conditions including increased blood pressure, high blood sugar, excess body fat around the waist, and abnormal cholesterol or triglyceride levels, which occur together can lead to significantly increased risk of heart disease, stroke, and diabetes. In addition, it is now known that diabetes increases risk of cancers of all sites by 30% except for prostatic cancer. Due to the rising incidence of diabetes, its chronic nature without an ultimate cure, and serious health implications associated with its complications, including but not limited to cardiovascular disease, kidney failure, cancer, blindness, leg amputation, which collectively carry enormous social and economic impact in a global scale, there exists an urgent need for new and effective means for treating and managing diabetes and associated diseases. The present invention fulfills this and other related needs.

BRIEF SUMMARY OF THE INVENTION

In a first aspect, the present invention provides an aryl pseudo-C-glycoside compound of formula (I):

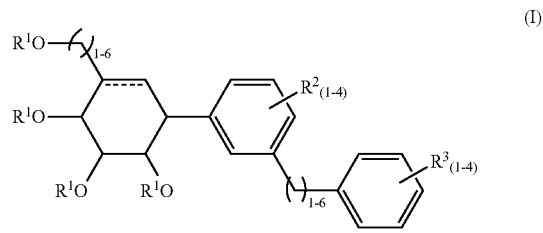

wherein: each $R^1$ is independently selected from the group consisting of H, $C_{1-6}$ alkyl, and $C_{1-6}$ alkyl-$C_{1-6}$ alkoxy; each $R^2$ is independently selected from the group consisting of H, halogen, $C_1$-$C_6$ alkyl, $C_3$-$C_6$ cycloalkyl, $C_2$-$C_{10}$ N-alkyl amine, $C_{1-6}$ haloalkyl, —CN, —OH, —$NR^4R^5$, —$C(O)R^4$, —$C(O)OR^4$, —$C(O)NR^4R^5$, —$SR^4$, and —$S(O)R^4$; each $R^3$ is independently selected from the group consisting of H, halogen, $C_1$-$C_6$ alkoxy, $C_3$-$C_6$ cycloalkyl, $C_2$-$C_{10}$ N-alkyl amine, —CN, $C_{1-6}$ haloalkoxy, —OH, —$NR^4R^5$, —$C(O)R^4$, —$C(O)OR^4$, —$C(O)NR^4R^5$, —$SR^4$, and —$S(O)R^4$; and $R^4$ and $R^5$ are each independently selected from the group consisting of hydrogen and $C_{1-6}$ alkyl.

In some embodiments, the aryl pseudo-C-glycoside compound has the structure of Formula II:

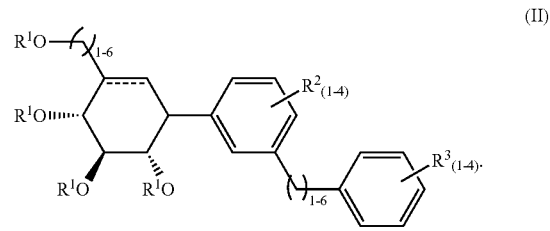

In some embodiments, the aryl pseudo-C-glycoside compound has the structure of Formula III:

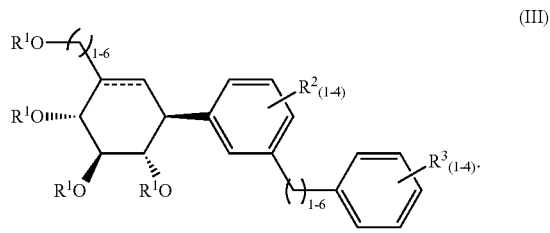

In some embodiments, the aryl pseudo-C-glycoside compound has the structure of Formula IV:

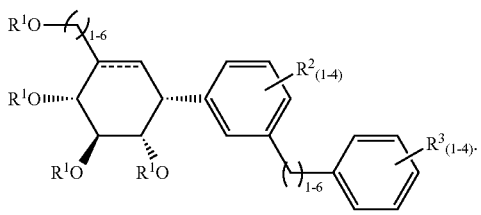

(IV)

In some embodiments, the aryl pseudo-C-glycoside compound has the structure of Formula V:

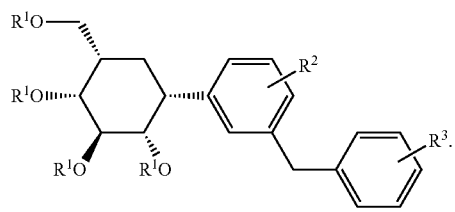

(V)

In some embodiments, the aryl pseudo-C-glycoside compound has the structure of Formula VI:

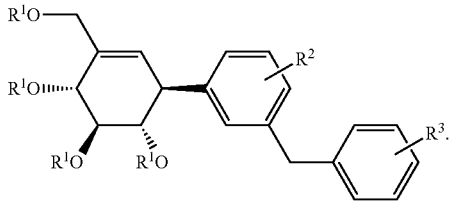

(VI)

In some embodiments, the aryl pseudo-C-glycoside compound has the structure of Formula VII:

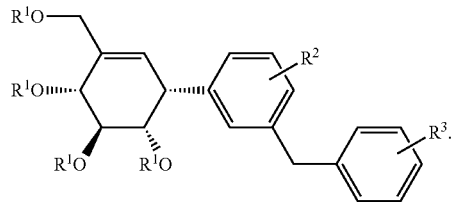

(VII)

In some embodiments, the aryl pseudo-C-glycoside compound has the structure of Formula IX:

(IX)

In some embodiments, the aryl pseudo-C-glycoside compound is selected from the group consisting of:

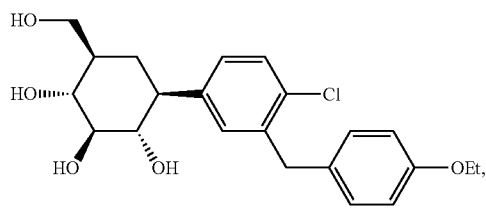

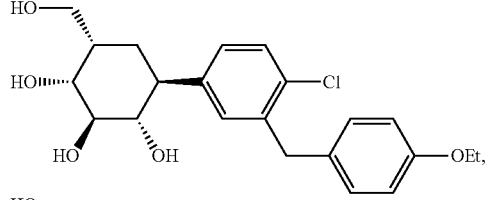

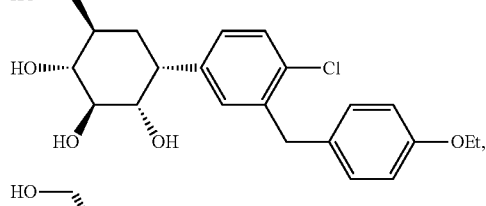

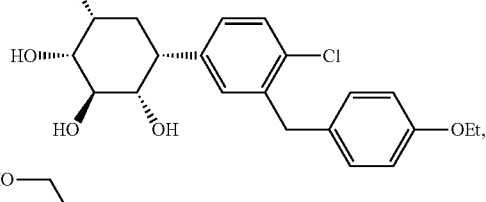

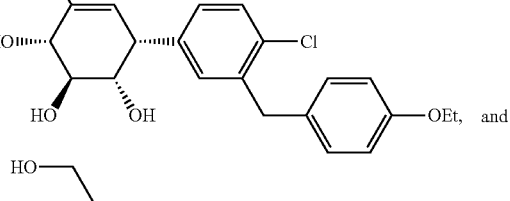

and

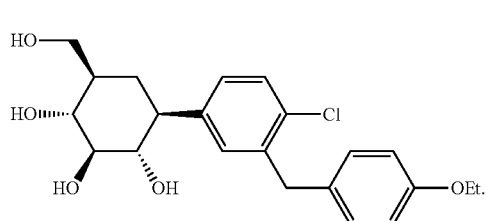

In some embodiments, the aryl pseudo-C-glycoside compound is

In a second aspect, the present invention provides a method of preparing an aryl pseudo-C-glycoside compound of Formula I:

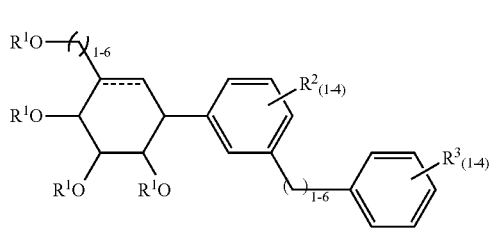

(I)

or salts thereof, the method comprising: forming a reaction mixture comprising a solvent, a palladium catalyst, a base, a compound of Formula X:

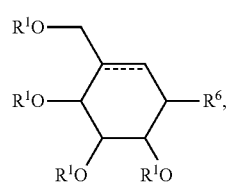

(X)

and a compound of Formula XI:

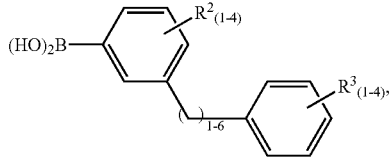

(XI)

under conditions suitable to prepare the compound of Formula I having a yield of at least 60%, wherein each $R^1$ is independently selected from the group consisting of H, $C_{1-6}$ alkyl, and $C_{1-6}$ alkyl-$C_{1-6}$ alkoxy; each $R^2$ is independently selected from the group consisting of H, halogen, $C_1$-$C_6$ alkyl, $C_3$-$C_6$ cycloalkyl, $C_2$-$C_{10}$ N-alkyl amine, $C_{1-6}$ haloalkyl, —CN, —OH, —NR$^4$R$^5$, —C(O)R$^4$, —C(O)OR$^4$, —C(O)NR$^4$R$^5$, —SR$^4$, and —S(O)R$^4$; each $R^3$ is independently selected from the group consisting of H, halogen, $C_1$-$C_6$ alkoxy, $C_3$-$C_6$ cycloalkyl, $C_2$-$C_{10}$ N-alkyl amine, —CN, $C_{1-6}$ haloalkoxy, —OH, —NR$^4$R$^5$, —C(O)R$^4$, —C(O)OR$^4$, —C(O)NR$^4$R$^5$, —SR$^4$, and —S(O)R$^4$; and $R^4$ and $R^5$ are each independently selected from the group consisting of hydrogen and $C_{1-6}$ alkyl.

In some embodiments, the solvent is selected from the group consisting of degassed 1,4-dioxane, methanol, ethanol, isopropanol, diethyl ether, acetonitrile, and tetrahydrofuran. In some embodiments, the solvent is degassed 1,4-dioxane. In some embodiments, the palladium catalyst is selected from the group consisting of Pd(dba)$_2$, Pd$_2$(dba)$_3$, Pd(PPh3)$_4$, Pd(OAc)$_2$, and PdCl$_2$(PPh3)$_2$. In some embodiments, the compound of Formula I is prepared with a yield of at least 75%. In some embodiments, the compound of Formula I is prepared with a yield of at least 85%.

In some embodiments, the compound of Formula I is prepared with less than 25% of a compound of Formula XII being present:

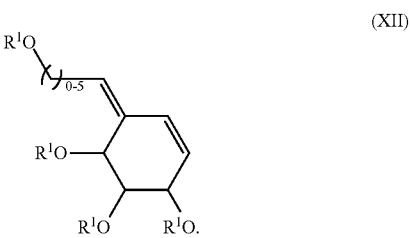

(XII)

In some embodiments, the compound of Formula V is prepared substantially free of the compound of Formula XII.

In some embodiments, the method comprises: forming the reaction mixture comprising degassed 1,4-dioxane, Pd(dba)$_2$, K$_2$CO$_3$, the compound of Formula X having the structure:

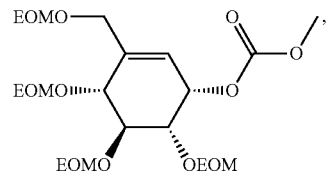

And the compound of Formula XI having the structure:

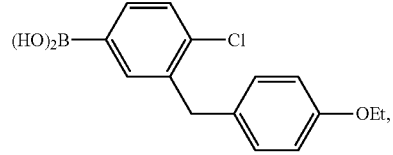 [SMILES: CCOc1ccc(Cc2cc(B(O)O)ccc2Cl)cc1]

under a nitrogen atmosphere, to prepare the compound of Formula I having the structure:

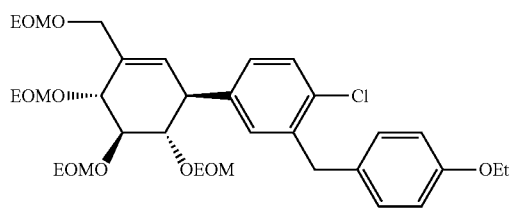

or salts thereof. In some embodiments, the method comprises: forming the reaction mixture comprising degassed 1,4-dioxane, Pd(dba)$_2$, K$_2$CO$_3$, the compound of Formula X having the structure:

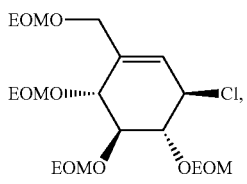

And the compound of Formula XI having the structure:

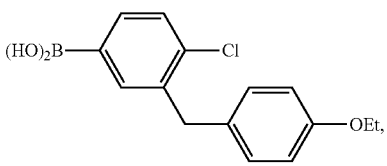 [SMILES: CCOc1ccc(Cc2cc(B(O)O)ccc2Cl)cc1]

under a nitrogen atmosphere, to prepare the compound of Formula I having the structure:

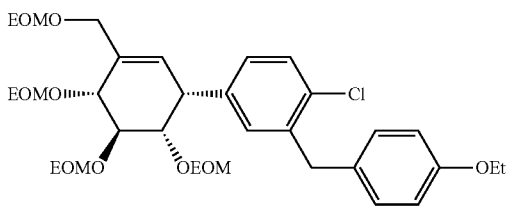

or salts thereof.

In a third aspect, the present invention provides a pharmaceutical composition comprising the aryl pseudo-C-glycoside compound of Formula I and a pharmaceutically acceptable excipient.

In a fourth aspect, the present invention provides a method for modulating sugar metabolism, comprising the step of administering to a patient in need thereof an effective amount of the aryl pseudo-C-glycoside compound of formula (I). In some embodiments, the patient has been diagnosed with diabetes. In some embodiments, the patient has been diagnosed with metabolic syndrome. In some embodiments, the patient has not been diagnosed with diabetes or metabolic syndrome but is at risk of developing diabetes or metabolic syndrome. In some embodiments, the compound is administered to the subject by oral ingestion, topical application, or injection. In some embodiments, the injection is subcutaneous, intravenous, intramuscular, or intraperitoneal injection.

DEFINITIONS

Figure 1:
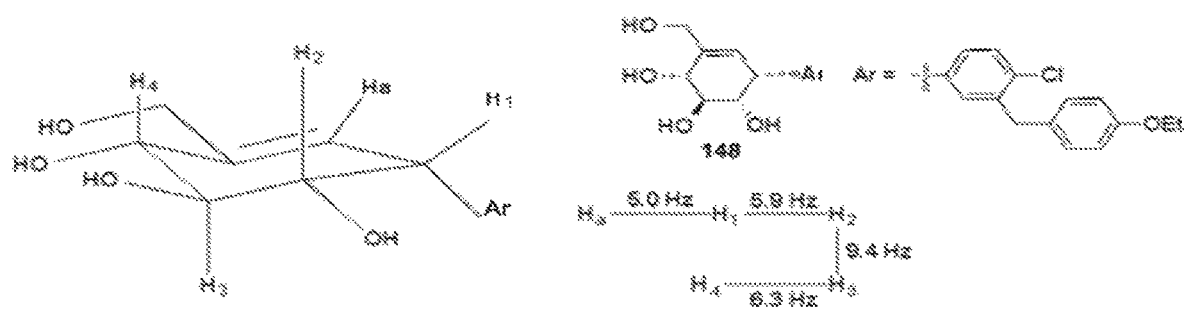
FIG. 1 shows the determination of stereochemistry of Tetraol 148 at C-1 after the coupling reaction.

As used herein, the term "halogen" refers to fluorine, chlorine, bromine and iodine.

The term "alkyl" as used herein refers to a straight or branched, saturated, aliphatic radical having the number of carbon atoms indicated. For example, $C_1$-$C_6$ alkyl includes, but is not limited to, methyl, ethyl, propyl, isopropyl, butyl, isobutyl, sec-butyl, tert-butyl, pentyl, isopentyl, hexyl, etc. Other alkyl groups include, but are not limited to heptyl, octyl, nonyl, decyl, etc. Alkyl can include any number of carbons, such as 1-2, 1-3, 1-4, 1-5, 1-6, 1-7, 1-8, 1-9, 1-10, 2-3, 2-4, 2-5, 2-6, 3-4, 3-5, 3-6, 4-5, 4-6 and 5-6. The alkyl group is typically monovalent, but can be divalent, such as when the alkyl group links two moieties together.

The term "alkoxy" as used herein refers to an alkyl group, as defined above, having an oxygen atom that connects the alkyl group to the point of attachment. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. The alkoxy groups can be further substituted with a variety of substituents described within. For example, the alkoxy groups can be substituted with halogens to form a "halo-alkoxy" group.

The term "haloalkyl" as used herein refers to alkyl as defined above where some or all of the hydrogen atoms are substituted with halogen atoms. Halogen (halo) preferably represents chloro or fluoro, but may also be bromo or iodo. For example, haloalkyl includes trifluoromethyl, fluoromethyl, 1,2,3,4,5-pentafluoro-phenyl, etc. The term "perfluoro" defines a compound or radical which has at least two available hydrogens substituted with fluorine. For example, perfluorophenyl refers to 1,2,3,4,5-pentafluorophenyl, perfluoromethane refers to 1,1,1-trifluoromethyl, and perfluoromethoxy refers to 1,1,1-trifluoromethoxy.

The term "cycloalkyl" as used herein refers to a saturated or partially unsaturated, monocyclic, fused bicyclic or bridged polycyclic ring assembly containing from 3 to 12 ring atoms, or the number of atoms indicated monocyclic rings include, for example, cyclopropyl, cyclobutyl, cyclopentyl, cyclohexyl, and cyclooctyl. Bicyclic and polycyclic rings include, for example, norbornane, decahydronaphthalene and adamantane. For example, $C_{3-8}$cycloalkyl includes cyclopropyl, cyclobutyl, cyclopentyl, cyclohexyl, cyclooctyl, and norbornane.

The term "amine" as used herein refers to an alkyl groups as defined within, having one or more amino groups. The amino groups can be primary, secondary or tertiary. The alkyl amine can be further substituted with a hydroxy group. Amines useful in the present invention include, but are not limited to, ethyl amine, propyl amine, isopropyl amine, ethylene diamine and ethanolamine. The amino group can link the alkyl amine to the point of attachment with the rest of the compound, be at the omega position of the alkyl group, or link together at least two carbon atoms of the alkyl group. One of skill in the art will appreciate that other alkyl amines are useful in the present invention.

The term "aryl" as used herein refers to a monocyclic or fused bicyclic, tricyclic or greater, aromatic ring assembly containing 6 to 16 ring carbon atoms. For example, aryl may be phenyl, benzyl or naphthyl, preferably phenyl. "Arylene" means a divalent radical derived from an aryl group. Aryl groups can be mono-, di- or tri-substituted by one, two or three radicals selected from alkyl, alkoxy, aryl, hydroxy, halogen, cyano, amino, amino-alkyl, trifluoromethyl, alkylenedioxy and oxy-$C_2$-$C_3$-alkylene; all of which are optionally further substituted, for instance as hereinbefore defined; or 1- or 2-naphthyl; or 1- or 2-phenanthrenyl. Alkylenedioxy is a divalent substitute attached to two adjacent carbon atoms of phenyl, e.g. methylenedioxy or ethylenedioxy. Oxy-$C_2$-$C_3$-alkylene is also a divalent substituent attached to two adjacent carbon atoms of phenyl, e.g. oxyethylene or oxypropylene. An example for oxy-$C_2$-$C_3$-alkylene-phenyl is 2,3-dihydrobenzofuran-5-yl.

As used herein, the term "heterocyclic ring" refers to a ring system having from 3 ring members to about 20 ring members and from 1 to about 5 heteroatoms such as N, O and S. Additional heteroatoms can also be useful, including, but not limited to, B, Al, Si and P. The heteroatoms can also be oxidized, such as, but not limited to, —S(O)— and —S(O)$_2$—. For example, heterocycle includes, but is not limited to, tetrahydrofuranyl, tetrahydrothiophenyl, morpholino, pyrrolidinyl, pyrrolinyl, imidazolidinyl, imidazolinyl, pyrazolidinyl, pyrazolinyl, piperazinyl, piperidinyl, indolinyl, quinuclidinyl and 1,4-dioxa-8-aza-spiro[4.5]dec-8-yl.

As used herein, "carbonyl" means a functional group composed of a carbon atom double-bonded to an oxygen atom: C=O. Carbonyls include without limitation, aldehydes, ketones, carboxylic acids, esters, and amides.

Unless specially mentioned the alkyl, alkoxy, haloalkyl cycloalkyl, haloalkoxy, and amine of the present invention can be substituted or unsubstituted. For example, $C_1$-$C_6$ alkyl group can be substituted by one, two, or three substitutes selected from hydroxyl, halogens, alkoxyl, dialkylamino, or heterocyclic ring such as morpholinyl, piperidinyl groups.

As used herein, "solvent" refers to polar, aprotic, protic, and non-polar solvents. Examples of solvents include compounds such as hexanes, benzene, toluene, diethyl ether, chloroform, methylene chloride, ethyl acetate, degassed 1,4-dioxane, water, tetrahydrofuran (THF), acetone, acetonitrile, DMF, DMSO, acetic acid, n-butanol, isopropanol, n-propanol, ethanol, methanol, formic acid, carbon tetrachloride, benzenethiol, chlorobenzene, cyclohexanethiol, 1-diethylaminoethanol, ethylene dichloride, ethylene glycol, xylene, 1,1,2,2-tetrachloroethane, phenol, acetic acid, 1-butanol, 2-butanol, 2-butanone, diglyme, dimethylether, dioxane, petroleum ether, N-methyl-2-pyrrolidinone (NMP), heptane, glycerin, HMPA (Hexamethylphosphorus triamide), MTBE (methyl t-butyl ether), nitromethane, pyrideine, 1-propanol, 2-propanol, and triethylamine.

As used herein, "palladium catalyst" refers to palladium based catalysts that are useful for the cross-coupling including Pd(dba)$_2$, Pd$_2$(dba)$_3$, Pd(PPh3)$_4$, Pd(OAc)$_2$, and PdCl$_2$(PPh3)$_2$.

As used herein, "base" refers to a substance which can accept protons or any chemical compound that yields hydroxide ions in solution. It is also commonly referred to as any substance that can react with an acid to decrease or neutralize its acidic properties, react with acids to form salts, and promote certain chemical reactions. Examples of bases include carbonates, non-nucleophilic bases, amine bases, halides, phosphates, hydroxides, disilylamides, and hydrides. The base chosen for a particular conversion depends on the nature of the starting materials, the solvent or solvents in which the reaction is conducted, and the temperature at which the reaction is conducted.

Bases useful in the present invention include carbonate salts such as potassium carbonate, potassium bicarbonate, sodium acetate, sodium carbonate, sodium bicarbonate, and cesium carbonate; halides including cesium fluoride; phosphates such as potassium phosphate, potassium dihydrogen phosphate, and potassium hydrogen phosphate; hydroxides such as lithium hydroxide, sodium hydroxide, and potassium hydroxide; disilylamides such as lithium hexamethyldisilazide, potassium hexamethyldisilazide, and sodium hexamethyldisilazide; and hydrides such as lithium hydride, sodium hydride, and potassium hydride.

As used herein, "non-nucleophilic base" refers to a chemical compound that functions as a base with no nucleophilicity. Preferably, the non-nucleophilic base does not react with the other compounds and reagents. A variety of non-nucleophilic bases are known to those of skill in the art. See, e.g., Richard C. Larock, in "Comprehensive Organic Transformation", 2$^{nd}$ edition, 1999. In some embodiments, the non-nucleophilic base is a tertiary amine. In one example, the tertiary amine is an aliphatic amine. In some embodiments, the tertiary amine is an aromatic amine. In some embodiments, the tertiary amine is a trialkylamine such as triethylamine or diisopropylethylamine.

As used herein, "amine bases" refers to primary, secondary, or tertiary amines, compounds of the formula R'R"R'"N where R', R", and R'" can be hydrogen or organic substituents. Alkylamines where one or more of the substituents is an aliphatic group can be used. Examples include octylamine, dipentylamine, triethylamine, diisopropylamine, and diisopropylethylamine, di-isopropyl ethyl amine, trimethylamine, quinuclidine, and tributylamine. Cycloalkylamines where one or more of the organic substituents is an alicyclic group such as cyclopropyl, cyclopentyl, or cyclooctyl. Monoaryl amines wherein the nitrogen is directly attached to an aromatic ring structure, which can have organic substituents, can also be used. Examples include N,N-methylphenylamine, aniline, and 4-methylaniline. Heterocyclic and substituted heterocyclic amines in which the amine nitrogen is incorporated into a ring structure such as in pyridine, pyrrolidine, and piperdine can also be used. Other examples of amines include imidazole, pyridazine, pyrimidine, and pyrazine and bicyclic amines such as 1,5-Diazabicyclo[4.3.0]non-5-ene (DBN) and 1,8-Diazabicyclo[5.4.0]undec-7-ene (DBU).

As used herein, "substantially free" refers to preferred negative limitations of the compositions of the present invention, and are directed to the amount or concentration of undesired compounds. Generally, the compositions preferably contain less than 5%, preferably less than 2%, more preferably less than 1%, even more preferably less than 0.5%, most preferably zero percent of such undesired compounds by weight of the composition.

As used in this application, an "increase" or a "decrease" refers to a detectable positive or negative change in quantity from a comparison control, e.g., an established standard control value. An increase is a positive change that is typically at least 10%, or at least 20%, or 50%, or 100%, and can be as high as at least 2-fold or at least 5-fold or even 10-fold of the control value. Similarly, a decrease is a negative change that is typically at least 10%, or at least 20%, 30%, or 50%, or even as high as at least 80% or 90% of the control value. Other terms indicating quantitative changes or differences from a comparative basis, such as "more," "less," "higher," and "lower," are used in this application in the same fashion as described above. In contrast, the term "substantially the same" or "substantially lack of change" indicates little to no change in quantity from the standard control value, typically within ±10% of the standard control value, or within ±5%, 2%, or even less variation from the standard control value.

The term "inhibiting" or "inhibition," as used herein, refers to any detectable negative effect on a target biological process, such as cellular signal transduction, cell proliferation, tumorigenicity, metastatic potential, sugar metabolism/blood sugar level, and onset or recurrence of a disease/condition. Typically, an inhibition is reflected in a decrease of at least 10%, 20%, 30%, 40%, or 50% in the target process (e.g., incidence of diabetes or fasting blood sugar level) upon application of an inhibitor, when compared to a control where the inhibitor is not applied.

The term "about," when used in the context of referring to a pre-determined value, describes a range of value that is +/−10% from the pre-determined value.

The term "treat" or "treating," as used in this application, describes to an act that leads to the elimination, reduction, alleviation, reversal, or prevention or delay of onset or recurrence of any symptom of a relevant condition, e.g., diabetes. In other words, "treating" a condition encompasses both therapeutic and prophylactic intervention against the condition.

The term "effective amount" as used herein refers to an amount of a given substance that is sufficient in quantity to produce a desired effect. For example, an effective amount of a novel compound of the present invention is the amount of said compound to achieve a decreased level of the target biological process, such that the symptoms, severity, and/or recurrence chances of a disease or condition involving such target process are reduced, reversed, eliminated, prevented, or delayed of the onset in a subject who has been given the compound for therapeutic purposes. An amount adequate to accomplish this is defined as the "therapeutically effective dose." The dosing range varies with the nature of the therapeutic agent being administered and other factors such as the route of administration and the severity of a subject's condition.

The term "subject" or "subject in need of treatment," as used herein, includes humans or animals in need medical attention due to risk of, or actual suffering from, a disease or condition involving inappropriate or undesirable sugar metabolism such as diabetes, pre-diabetic high blood sugar, and metabolic syndrome. Subjects also include individuals currently undergoing therapy that seek manipulation of the therapeutic regimen. Subjects or individuals in need of treatment include those that demonstrate symptoms of such disease or condition or are at risk of suffering from the disease/condition or its symptoms. For example, a subject in need of treatment includes individuals with a genetic predisposition or family history for diabetes or metabolic syndrome, those that have suffered relevant symptoms in the past, those that have been exposed to a triggering substance or event, as well as those suffering from chronic or acute symptoms of the condition. A "subject in need of treatment" may be at any age of life.

DETAILED DESCRIPTION OF THE INVENTION

I. Introduction

As discussed above, there is a need for novel therapeutic agents capable of effectively treating and managing diabetes and associated diseases. The present invention generally provides compositions and methods of preparing novel aryl pseudo-C-glycoside compounds useful for treating and managing diabetes and associated diseases. As demonstrated below, the Suzuki-type coupling between compounds of Formula XI and compounds of Formula X is an important reaction that allows for a stepwise controlled preparation of aryl pseudo-C-glycoside compounds.

Sodium-dependent glucose cotransporter 2 (SGLT2) is a high-capacity, low-affinity transporter protein found mainly in the $S^1$ domain of the proximal tubule of kidneys. It is responsible for about 90% of renal glucose reabsorption.[1] On the other hand, sodium-dependent glucose cotransporter 1 (SGLT1) is a low-capacity, high-affinity glucose transporter, which is located not only in kidneys, but also in the gut and other tissues.[2] Inhibition of SGLT2 can help reduce blood glucose level in diabetes patients by promoting urinary glucose excretion, whereas inhibition of SGLT1 may lead to delayed absorption of carbohydrates[3] or diarrhoea.[4] Selective inhibition of SGLT2 over SGLT1 is thus highly desirable. In recent years, SGLT2 inhibition has emerged as a promising tool to fight against T2DM via an insulin-independent mechanism.[3-5] The current SGLT2 inhibitors could be classified according to their molecular structures. To date, most of them are carbohydrate-based small molecules in which O-, C- and N-glycosides are dominated. The present invention provides a new class of metabolically stable SGLT2 inhibitors that can be prepared by a Suzuki-type coupling between compounds of Formula XI and compounds of Formula X.

II. Synthesis of Aryl Pseudo-C-Glycoside Compound Starting Materials

Apart from the methods that are known in the literature or exemplified in the experimental procedures in the standard methods, the starting materials used for the preparation of compounds of Formula I mentioned in this invention can be prepared by the following methods. Therefore, the following methods are used for illustration and are not limited to the listed compounds or any particular substituent.

A. Preparation of Compounds of Formula XI Including Aryl Boronic Acid 124 and Pinacol Boronic Ester 147 as Coupling Partners The first task was to prepare the aglycon of dapagliflozin for the subsequent allyl-aryl coupling reaction. Bromochlorobenzene 143 was converted into aryl boronic acid 124 by a one-pot three-step synthetic sequence. (Scheme 1) Lithium-bromide exchange in a mixture of THF and toluene yielded the lithiated intermediate 144. Electrophilic trapping of 144 by triisopropyl borate afforded boronic ester 145 which was hydrolyzed easily upon acidic quenching. Thus, aryl boronic acid 124 and its corresponding boroxine 146 were obtained in 51% yield (based on monomer 124).

Scheme 1

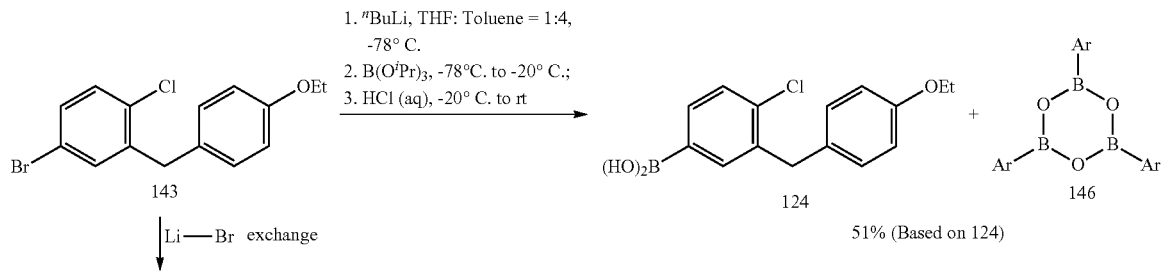

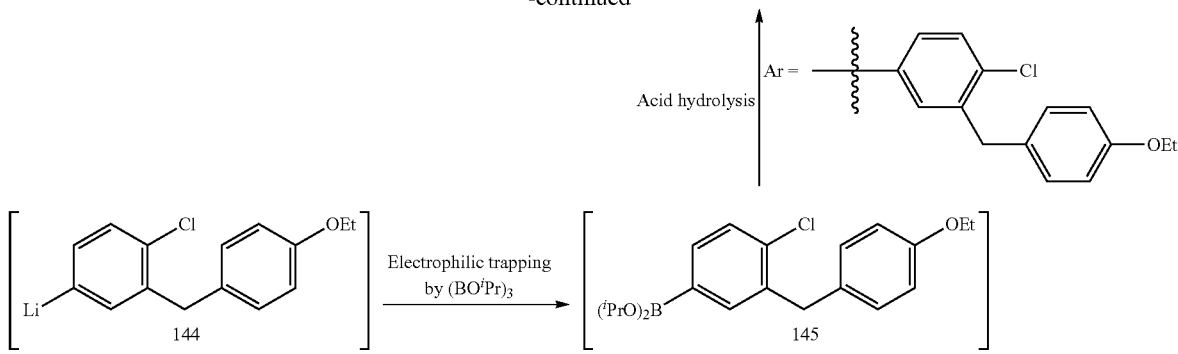

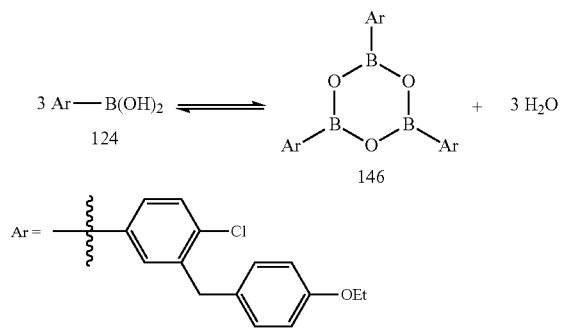

It was found that aryl boronic acid 124 dehydrated rapidly to form the trimeric boroxine 146 upon storage. (Scheme 2) Thus, the purity of boronic acid 124 varied from time to time. However, as boroxines were reported to behave similarly to their parent boronic acids, the mixture of 124 and 146 was used directly for the coupling reaction.[6]

Scheme 2

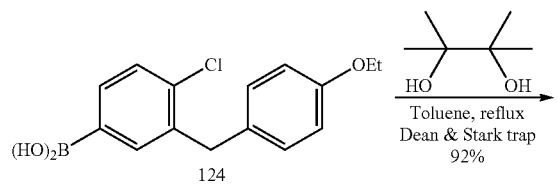

Characterization of aryl boronic acid 124 was not trivial due to the unavoidable contamination from boroxine 146. It was then decided to synthesize its pinacol boronic ester 147 for the sake of characterization. (Scheme 3)

Scheme 3

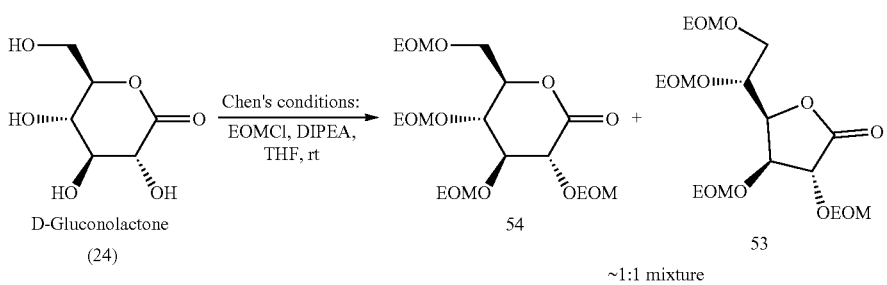

In refluxing toluene, aryl boronic acid 124 was converted to its pinacol boronic ester 147 in 92% yield. A Dean and Stark trap helped remove the water generated from the reaction, thus driving the equilibrium position of the reaction towards the product side. The pinacol boronic ester 147 was then characterized by $^{11}B$, $^{1}H$, and $^{13}C$ NMR spectroscopy. It should be noticed that 147 could also be used as a coupling partner in the subsequent cross-coupling reaction.

B. Preparation of Compounds of Formula X via the Carbocyclization of D-Gluconolactone: Carbocyclic α-Allylic Alcohol 52 and Allylic Chloride 60

In order to prepare a large quantity of 52, the exploration of a more efficient and scalable synthetic route was investigated. The first step yielded a significant amount of side product, a five-membered ring lactone 53, along with the desired six-membered ring lactone 54 as a nearly 1:1 mixture (Scheme 6). This seemingly simple transformation significantly lowered the efficiency of our carbocyclization sequences. Thus, a more synthetically useful hydroxyl group protection condition was highly sought-after. It was postulated that the use of a more hindered, non-nucleophilic base could minimize the formation of the undesired five-membered lactone 53. Therefore, attempts were made to perform the protection reaction using 2,6-lutidine as the base and in the presence of various solvents. Fortunately, $CH_2Cl_2$ was identified as the optimal reaction solvent in which the desired six-membered ring lactone 54 was obtained in 93% yield. (Scheme 4)

Scheme 4

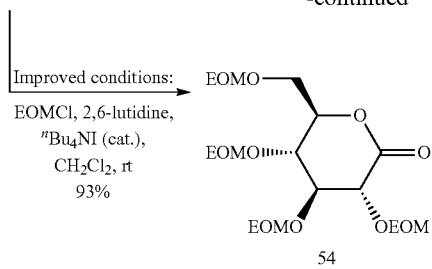

With the protected lactone 54 in hand, nucleophilic addition of a lithiated phosphonate at low temperature, yielded phosphonate 55. Sodium borohydride reduction of the lactol moiety in 55 gave diol 56 in a good yield. (Scheme 5) It was found that the protection/nucleophilic addition/reduction sequence could be performed in a telescoping manner over these three steps. Not only did this method ease the purification procedures, it also improved the overall yield of the three transformations. Thus, diol 56 was rapidly prepared for the subsequent carbocyclization reaction.

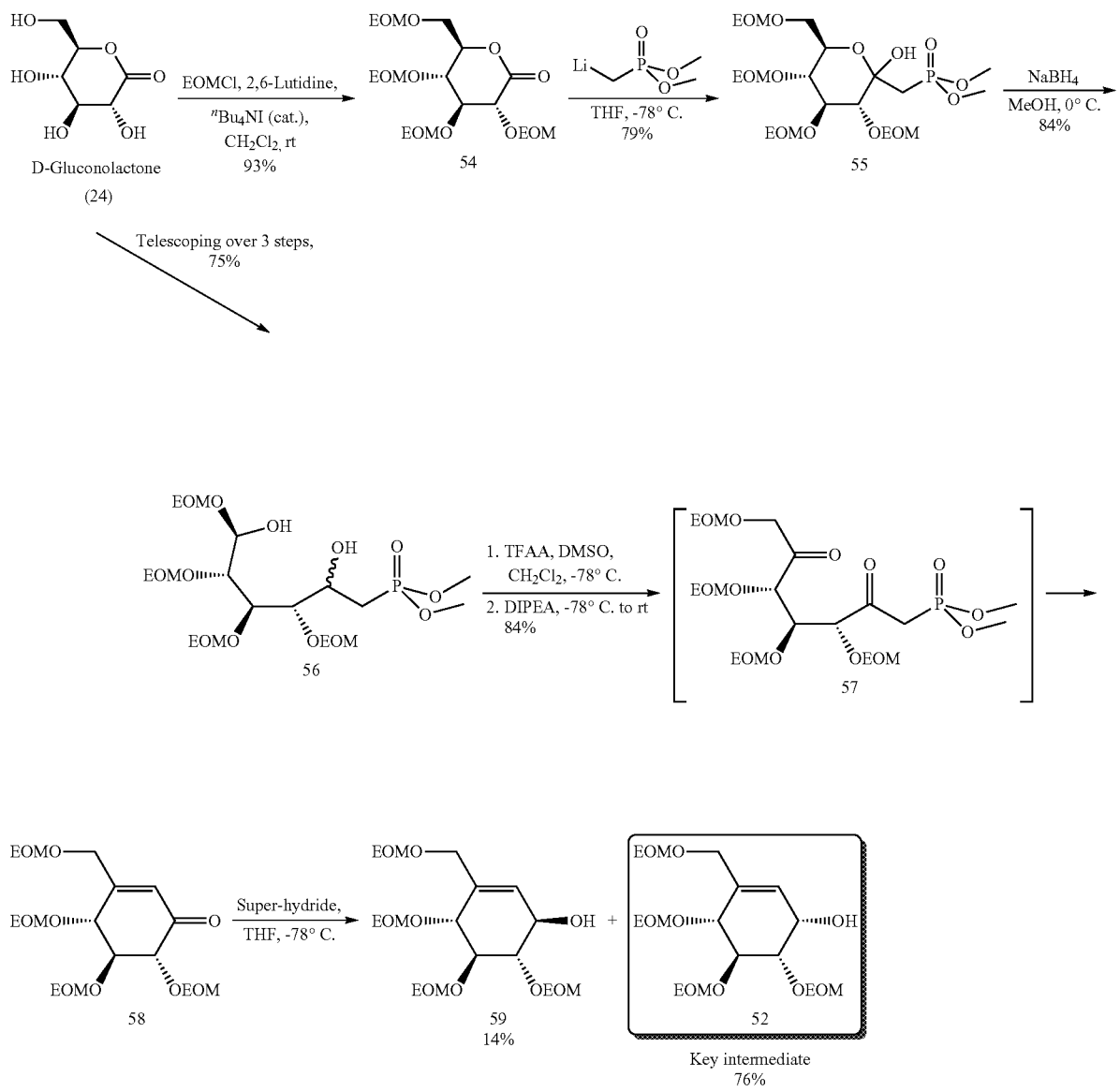

The key carbocyclization sequence involved the Swern oxidation of diol 56 and the concomitant Horner-Wadsworth-Emmons (HWE) olefination. It was achieved by treating a dichloromethane solution of diol 56 with TFAA and DMSO at −78° C., followed by using DIPEA as the base to promote both the oxidation step and HWE olefination step. The temperature and time control of this reaction was the key to obtain a good yield of enone 58. It was postulated that diketone 57 was formed as an intermediate after adding the first portion of DIPEA at −78° C. The gradual increase in reaction temperature and the addition of the second portion of DIPEA led to the formation of enone 58. It should also be noticed that prolonged stirring of the reaction mixture at room temperature led to the formation of some unidentified side products.

With enone 58 in hand, stereoselective hydride reduction by Super-hydride was carried out to afford β-allylic alcohol 59 and α-allylic alcohol 52 in 14% and 76% yield respectively. This α-allylic alcohol 52 served as an important common intermediate for the subsequent transformations towards O-, C- and N-aryl pseudo-glycosides.

Attention then turned to the preparation of allylic chloride 60, one of the coupling partners in the allylic substitution reaction. Various chlorination methods were attempted to chlorinate the key allylic alcohol 52. The results are summarized in Table 1.

Although this transformation can appear trivial it proved to be quite problematic. Attempts to chlorinate allylic alcohol 52 via standard chlorination methods such as the use of NCS/PPh$_3$ (entry 1, Table 1)[7] and CCl$_4$/PPh$_3$/imidazole (entry 2)[8] systems were fruitless. We next tried to convert the hydroxyl group to a mesylate group for subsequent nucleophilic substitution. However, the mesylate intermediate decomposed immediately upon workup (entry 3). Thus, one-pot mesylation/substitution reactions were attempted by adding various chloride sources to the reaction mixture. The use of LiCl as the chloride source gave no desired products (entry 4, 5). The sequential mesylation/S$_N$2 substitution with "Bu$_4$NCl gave the desired allylic chloride 60 in 58% yield (entry 6). The best reaction condition was the one-pot mesylation/substitution with "Bu$_4$NCl, with the use of Et$_3$N as the base (entry 8). Although 60 was obtained in a good yield, a diene side product was always isolated after the reaction, indicating that the mesylate intermediate was prone to base-promoted elimination.

C. Preparation of Compounds of Formula X via the Carbocyclization of D-Gluconolactone: Carbocyclic β-Allylic Alcohol 52 and Allylic Carbonate 81

Attention was then turned to the preparation of β-allylic Alcohols by reviewing the previously developed a method to carbocyclized D-gluconolactone (38) into a cyclic allylic alcohol in five steps.[9,10] (Scheme 6) The reaction condition was further optimized during this research project. Hydroxyl groups of D-gluconolactone (38) were first protected. Global etherification of D-gluconolactone (38) was carried out by using ethoxymethyl (EOM) chloride and 2,6-lutidine in CH$_2$Cl$_2$ at room temperature for 60 h to yield lactone 82. Prolonged reaction time was required as every ethoxymethyl ether moiety introduced would increase the steric hindrance of the molecule. Diisopropylamine was first reacted with nBuLi in THF at −78° C. for 30 minutes to generate lithium diisopropylamide (LDA), followed by addition of dimethyl methylphosphonate to prepare the lithiated dimethyl methylphosphonate. Lactone 82 was then reacted with the lithiated dimethyl methylphosphonate in THF at −78° C. for 30 minutes to give lactol 83. It is important to keep the lithiated dimethyl methylphosphonate at low temperature during the reaction as it would decompose if it is warmed up. Freshly prepared lithiated dimethyl methylphosphonate should be kept in a flask at −78° C. and added dropwise to lactone 82 in THF at −78° C. through a wrapped cannula. Lactol 83 was then reduced by using sodium borohydride in MeOH at 0° C. for 1 h to give diol 84. It was founded that purification was not required before we got diol 84. For the first two steps, only workup and evaporation of solvent was needed and the crude could be carried on to the next step directly to save time for purification. After sodium borohydride reduction, the product was purified by column chromatography and diol 84 was obtained in 91% over three steps.

Scheme 6

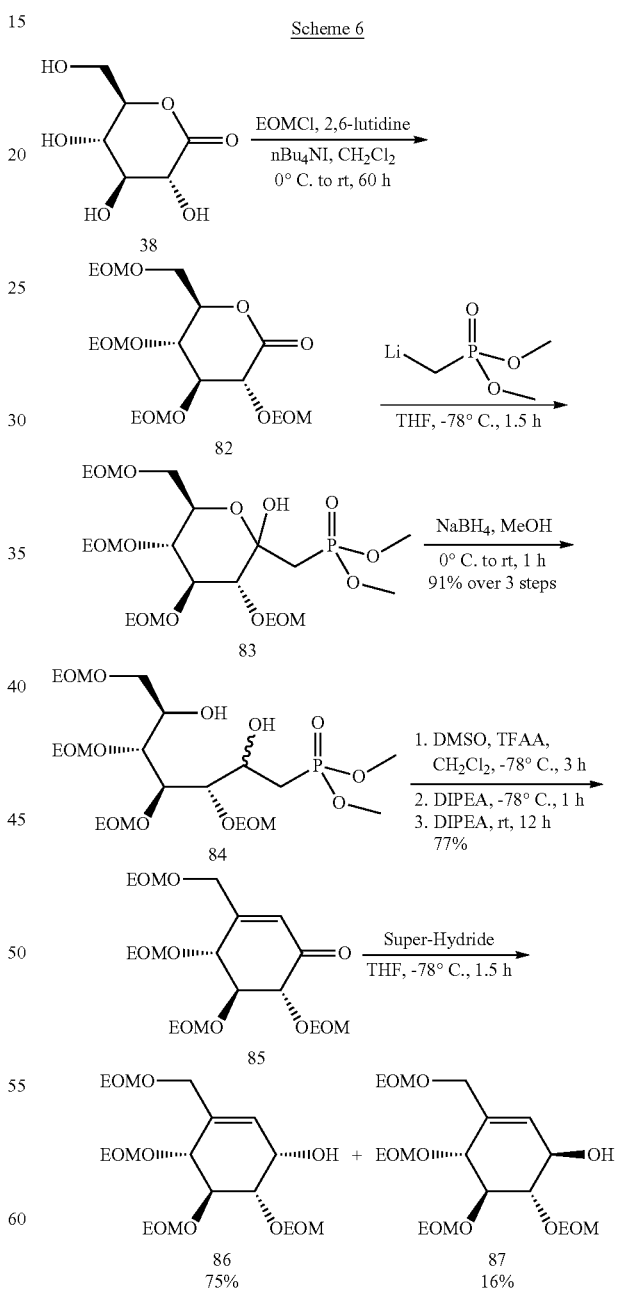

The next step is the key carbocyclization step. A one-pot Swern oxidation/intramolecular Horner-Wadsworth-Emmons (HWE) olefination was carried out on diol 84. Swern oxidation on diol 84 was first carried out by using trifluoroacetic anhydride (TFAA) with DMSO in $CH_2Cl_2$ at $-78°$ C. N,N-Diisopropylethylamine (DIPEA) was added at $-78°$ C. to deprotonated the alkoxysulfonium ion. The reaction mixture was then warmed up to room temperature and extra DIPEA was added to carry out the HWE olefination. Cyclic enone 85 was obtained in good yield. After that a stereoselective 1,2-reduction was carried out on the cyclic enone 85 by using superhydride in THF at $-78°$ C. Cyclic α-allylic alcohol 86 and cyclic β-allylic alcohol 87 were obtained in 75% and 16% yield respectively.

According to the reported Suzuki-type aryl-allyl coupling reaction mentioned above, steric hindrance and electron density of the allylic coupling partner would be the main reason to affect the efficiency of the coupling reaction.[11-18] Sterically hindered or electron rich cyclic allylic substrate, generally, give a poorer result, thus, the previously prepared cyclic α-allylic alcohol 86 would not be a desirable coupling partner. Instead of cyclic allylic carbonate 81, we first wanted to prepare the more reactive cyclic allylic chloride 109. Since the transformation of hydroxyl group to chloride generally involved a $S_N2$ mechanism, various chlorination methods were attempted on β-allylic alcohol 87 and the results are listed in Table 2.

Chlorination of cyclic β-allylic alcohol 87 was first attempted by using thionyl chloride. However, reactions in $Et_2O$ (Entry 1, Table 2) or with pyridine in $Et_2O$ (Entry 2, Table 2) both resulted in decomposition of staring material. Chlorination of β-allylic alcohol 87 by neat $SOCl_2$ (Entry 3, Table 2) was attempted as well but it resulted in a very complex reaction mixture. One-pot mesylation/chlorination were also tried. Sequential addition of mesyl chloride and n-tetrabutylammonium chloride or addition of mesyl chloride to a pre-mixed reaction mixture in $Et_3N$ and $CH_2Cl_2$ (Entry 4 and 5, Table 2) both resulted in decomposition of starting material. Instead of $Et_3N$, one-pot mesylation/chlorination was also attempted in neat pyridine, which served as a base and solvent as well, but again it resulted in decomposition of starting material.

The result was out of expectation. Cyclic α-allylic alcohol 86 was successfully converted to the corresponding cyclic allylic chloride 110 (Scheme 7) by the same condition as used in entry 5, Table 2.[19] The cyclic allylic chloride 109 was relatively unstable when compared to cyclic allylic chloride 110. The chloride at C1 in 109 is in a pseudo-axial position which might allow other nucleophilic attack or elimination occur easily and thus promoted further decomposition.

Therefore, preparation of a relatively more stable coupling partner was attempted. Various conversions of α-allylic alcohol 86 to cyclic allylic carbonate 81 were tried and the results are listed in Table 3.

α-Allylic alcohol 86 was first tried to react with methyl chloroformate and $Et_3N$ in $CH_2Cl_2$ to obtain cyclic allylic carbonate 81. A large amount of starting material was observed on TLC even after the addition of extra chloroformate and $Et_3N$. Cyclic allylic carbonate 81 was obtained in low yield. (Entry 1, Table 3) It was thought to be the moisture in the system prohibited the reaction. So a trial with the condition of entry 1 together with the addition of 3 Å MS was carried out. The result, however, was not improved. (Entry 2, Table 3) Thereafter, pyridine was used as base to promote the conversion with a surprising result. Using methyl chloroformate with pyridine in $CH_2Cl_2$ yield cyclic allylic carbonate 81 in 65% (BORSM 80%) while still a significant amount of starting material was left. (Entry 3, Table 3) The result was further improved by using neat pyridine to replace $CH_2Cl_2$; cyclic allylic carbonate 81 was obtained in 74% (BORSM 92%), but again, starting material was observed in the reaction mixture even after the addition of extra methyl chloroformate. (Entry 4, Table 3) Stronger base was used to try to consume all the staring material; however, deprotonation by nBuLi followed by subsequent addition of methyl chloroformate in THF only gave cyclic allylic carbonate 81 in moderate yield. (Entry 5, Table 3)

III. Suzuki-Type Coupling Between Compounds of Formula XI and Compounds of Formula X In some embodiments, the present invention provides a method of preparing an aryl pseudo-C-glycoside compound of Formula I:

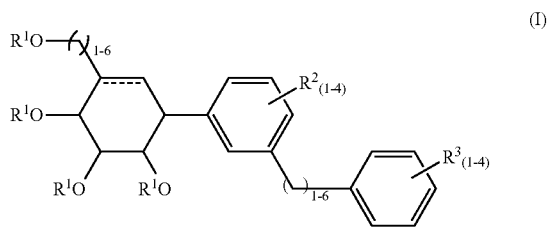

or salts thereof, the method comprising: forming a reaction mixture comprising a solvent, a palladium catalyst, a base, a compound of Formula X:

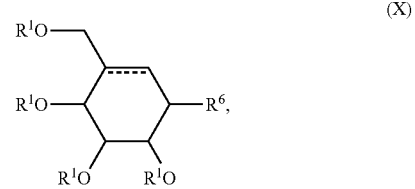

Scheme 7

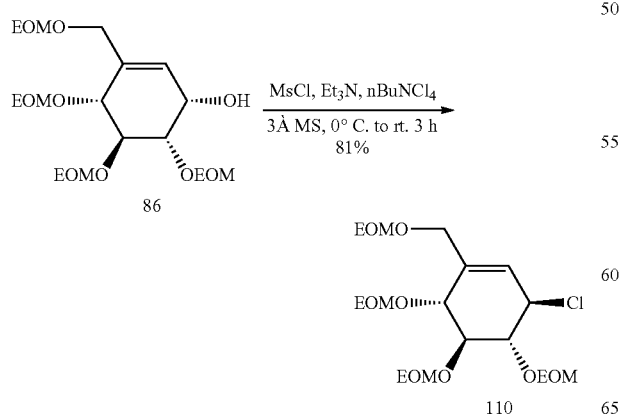

and a compound of Formula XI:

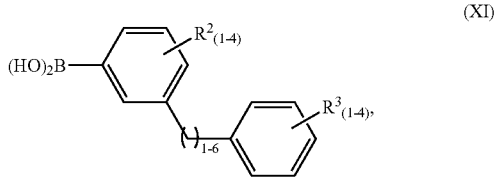

under conditions suitable to prepare the compound of Formula I having a yield of at least 60%, wherein each $R^1$ is independently selected from the group consisting of H, $C_{1-6}$ alkyl, and $C_{1-6}$ alkyl-$C_{1-6}$ alkoxy; each $R^2$ is independently selected from the group consisting of H, halogen, $C_1$-$C_6$ alkyl, $C_3$-$C_6$ cycloalkyl, $C_2$-$C_{10}$ N-alkyl amine, $C_{1-6}$ haloalkyl, —CN, —OH, —$NR^4R^5$, —$C(O)R^4$, —$C(O)OR^4$, —$C(O)NR^4R^5$, —$SR^4$, and —$S(O)R^4$; each $R^3$ is independently selected from the group consisting of H, halogen, $C_1$-$C_6$ alkoxy, $C_3$-$C_6$ cycloalkyl, $C_2$-$C_{10}$ N-alkyl amine, —CN, $C_{1-6}$ haloalkoxy, —OH, —$NR^4R^5$, —$C(O)R^4$, —$C(O)OR^4$, —$C(O)NR^4R^5$, —$SR^4$, and —$S(O)R^4$; and $R^4$ and $R^5$ are each independently selected from the group consisting of hydrogen and $C_{1-6}$ alkyl.

In some embodiments, the compounds of Formula I are prepared with a yield of at least 70%, 72%, 74%, 75%, 76%, 78%, 80%, 82%, 84%, 85%, 86%, 88%, 90%, 92%, 94%, 95%, 96%, 97%, 98% or 99%. In some embodiments, the compound of Formula I is prepared with a yield of at least 75%. In some embodiments, the compound of Formula I is prepared with a yield of at least 85%.

Bases useful in the present invention include carbonates, non-nucleophilic bases, amine bases, halides, phosphates, hydroxides, disilylamides, and hydrides. The base chosen for a particular conversion depends on the nature of the starting materials, the solvent or solvents in which the reaction is conducted, and the temperature at which the reaction is conducted.

Bases useful in the present invention include carbonate salts such as potassium carbonate, potassium bicarbonate, sodium acetate, sodium carbonate, sodium bicarbonate, and cesium carbonate; halides including cesium fluoride; phosphates such as potassium phosphate, potassium dihydrogen phosphate, and potassium hydrogen phosphate; hydroxides such as lithium hydroxide, sodium hydroxide, and potassium hydroxide; disilylamides such as lithium hexamethyldisilazide, potassium hexamethyldisilazide, and sodium hexamethyldisilazide; and hydrides such as lithium hydride, sodium hydride, and potassium hydride.

A variety of non-nucleophilic bases are useful in the present invention and known to those of skill in the art. See, e.g., Richard C. Larock, in "Comprehensive Organic Transformation," 2nd edition, 1999. In some embodiments, the non-nucleophilic base is a tertiary amine. In some embodiments, the tertiary amine is an aliphatic amine. In some embodiments, the tertiary amine is an aromatic amine. In some embodiments, the tertiary amine is a trialkylamine such as triethylamine or diisopropylethylamine.

Amine bases useful in the present invention include primary, secondary, or tertiary amines, compounds of the formula R'R"R'"N where R', R", and R'" can be hydrogen or organic substituents. Alkylamines where one or more of the substituents is an aliphatic group can be used. Examples include octylamine, dipentylamine, triethylamine, diisopropylamine, and diisopropylethylamine, di-isopropyl ethyl amine, trimethylamine, quinuclidine, and tributylamine. Cycloalkylamines where one or more of the organic substituents is an alicyclic group such as cyclopropyl, cyclopentyl, or cyclooctyl. Monoaryl amines wherein the nitrogen is directly attached to an aromatic ring structure, which can have organic substituents, can also be used. Examples include N,N-methylphenylamine, aniline, and 4-methylaniline. Heterocyclic and substituted heterocyclic amines in which the amine nitrogen is incorporated into a ring structure such as in pyridine, pyrrolidine, and piperdine can also be used. Other examples of amines include imidazole, pyridazine, pyrimidine, and pyrazine and bicyclic amines such as 1,5-Diazabicyclo[4.3.0]non-5-ene (DBN) and 1,8-Diazabicyclo[5.4.0]undec-7-ene (DBU).

In some embodiments, the base is a carbonate salt. In some embodiments, the carbonate salt is selected consisting of potassium carbonate, potassium bicarbonate, sodium acetate, sodium carbonate, sodium bicarbonate, and cesium carbonate. In some embodiments, the base is potassium carbonate.

Solvents useful in the present invention include polar, aprotic, protic, and non-polar solvents. Examples of solvents useful in the present invention include degassed 1,4-dioxane, hexanes, benzene, toluene, diethyl ether, chloroform, methylene chloride, ethyl acetate, 1,4-dioxane, water, tetrahydrofuran (THF), acetone, acetonitrile, DMF, DMSO, acetic acid, n-butanol, isopropanol, n-propanol, ethanol, methanol, formic acid, carbon tetrachloride, benzenethiol, chlorobenzene, cyclohexanethiol, 1-diethylaminoethanol, ethylene dichloride, ethylene glycol, xylene 1,1,2,2-tetrachloroethane, phenol, acetic acid, 1-butanol, 2-butanol, 2-butaone, diglyme, dimethylether, dioxane, petroleum ether, (NMP) N-methyl-2-pyrrolidinone, heptane, glycerin, HMPA (Hexamethylphosphorus triamide), MTBE (methyl t-butyl ether), nitromethane, pyrideine, 1-propanol, 2-propanol, and triethylamine.

In some embodiments, the solvent is selected from the group consisting of degassed 1,4-dioxane, methanol, ethanol, isopropanol, diethyl ether, acetonitrile, and tetrahydrofuran. In some embodiments, the solvent is degassed 1,4-dioxane.

In some embodiments, the palladium catalyst is selected from the group consisting of $Pd(dba)_2$, $Pd_2(dba)_3$, Pd (PPh3)$_4$, $Pd(OAc)_2$, and $PdCl_2(PPh3)_2$.

In some embodiments, the compound of Formula I is prepared with less than 25% of a compound of Formula XII being present:

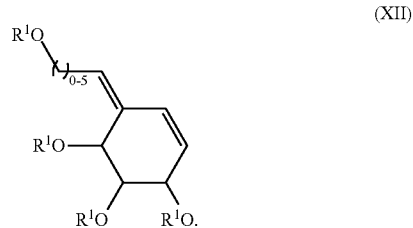

In some embodiments, the compound of Formula V is prepared substantially free of the compound of Formula XII.

In some embodiments, the method comprises: forming the reaction mixture comprising degassed 1,4-dioxane, Pd (dba)$_2$, $K_2CO_3$, the compound of Formula X having the structure:

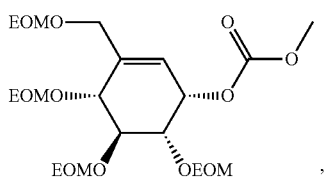

And the compound of Formula XI having the structure:

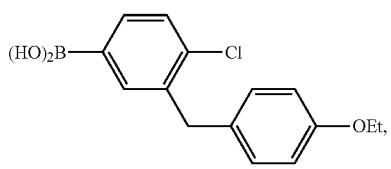 [SMILES: CCOc1ccc(Cc2cc(B(O)O)ccc2Cl)cc1]

under a nitrogen atmosphere, to prepare the compound of Formula I having the structure:

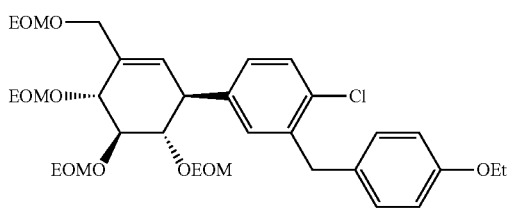

or salts thereof. In some embodiments, the method comprises: forming the reaction mixture comprising degassed 1,4-dioxane, Pd(dba)$_2$, K$_2$CO$_3$, the compound of Formula X having the structure:

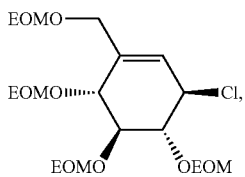

And the compound of Formula XI having the structure:

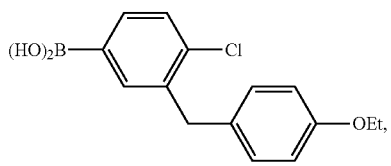

under a nitrogen atmosphere, to prepare the compound of Formula I having the structure:

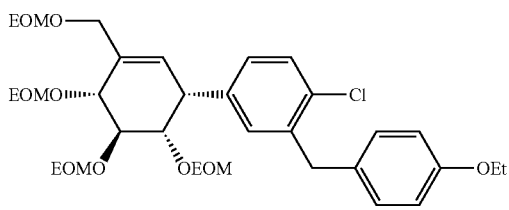

or salts thereof.

The method of preparing the compound of Formula I occurs under suitable reaction conditions. Suitable reaction conditions include all reaction conditions suitable for preparing compounds of Formula I. In some embodiments, reaction conditions include reagents, time, temperature, pressure, and stoichiometric ratios. One of skill in the art will appreciate that changes and modifications to the reaction conditions may be practiced within the scope of the appended claims.

The reaction mixtures of the method for preparation of Formula I can be at any suitable temperature. For example, the temperature of the reaction mixture can be of from about 0° C. to about 200° C., such as at about 0, 5, 10, 15, 20, 25, 30, 35, 40, 45, 50, 55, 60, 62, 64, 65, 66, 70, 75 or about 80° C. In some embodiments, the temperature of the reaction mixture can be from about 5° C. to about 35° C., or of from about 10° C. to about 30° C., or of from about 15° C. to about 25° C. In some embodiments, the temperature of the reaction mixture can be about 20° C.

The reaction mixtures for preparation of Formula I of the method can be at any suitable pressure. For example, the reaction mixture can be at atmospheric pressure or above atmospheric pressure. Pressures greater than atmospheric pressure can be achieved by using a pressure vessel and pressurizing with a suitable gas, or using a closed vessel that is then heated. The reaction mixtures can be also be exposed to any suitable environment, such as atmospheric gases, or inert gases such as nitrogen or argon. In some embodiments, the inert gas exposed to the reaction mixture is nitrogen.

The reaction mixtures of the method for preparation of Formula I can also be agitated by any suitable means. For example, the reaction mixtures can be stirred, shaken, vortexed, or others.

Each reaction mixture of the method for preparation of Formula I can be mixed for any suitable period of time from minutes to hours. For example, the reaction mixture can be mixed for about 5 minutes, or 10, 15, 20, 30, 40, 50, 60, 70, 80, 90, 100, 110, or 120 minutes, or for about 3, 4, 6, 12, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, or 80 hours.

A. Suzuki-Type Coupling Between Aryl Boronic Acid Derivatives and Allylic Chloride 60

With access to the derivatives of aryl boronic acid 124, the next objective was to perform the Suzuki-type allyl-aryl cross-coupling using allylic chloride 60 as the electrophile. The results of the coupling reaction are summarized in Table 4. The reaction was first conducted under the optimized conditions of the model study. However, boronic acid 124 was found to be insoluble in CH$_3$CN, and thus CHCl$_3$ was used as the solvent instead (entries 1-3, Table 4). In CHCl$_3$, a low yield of coupled product 125 was obtained by using K$_2$CO$_3$ as the base (entry 1, Table 4). So other additives such as K$_3$PO$_4$.3H$_2$O or KF were used, and K$_3$PO$_4$.3H$_2$O was found to promote the reaction effectively (entries 2 and 3, Table 4). 1,4-dioxane was also explored as a solvent for this transformation. Surprisingly, the use of K$_2$CO$_3$ in 1,4-dioxane gave the desired coupled product 125 in 88% yield (entry 5, Table 4).

On the other hand, pinacol boronic ester 147 also performed well as a coupling partner in this reaction. The use of K$_3$PO$_4$.3H$_2$O in 1,4-dioxane furnished the coupled product 125 in 71% yield (entry 6, Table 4). The presence of water in the reaction mixture did not retard the reaction which eased the preparation of our target molecule.

Thus, the newly developed Suzuki-type allyl-aryl coupling effectively afforded 125 both regio- and stereoselectively. (Scheme 8) Acid hydrolysis of 125 gave tetraol 148 as a carbocyclic allylic analogue of dapagliflozin.

Scheme 8

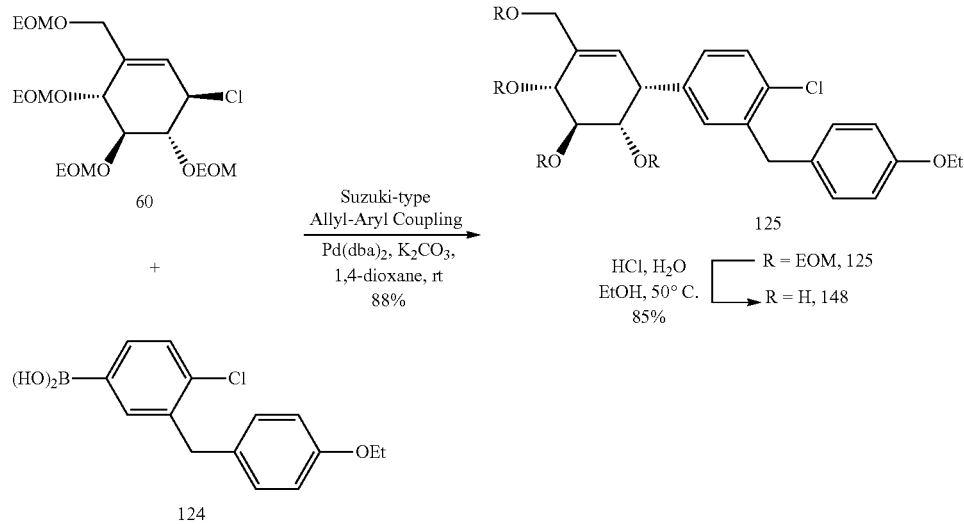

Tetraol 148 also served the purpose of the determination of stereochemistry at C-1 after the coupling reaction (FIG. 1). The coupling constant between $H_1$ and $H_2$ ($J_{1,2}$) was 5.9 Hz, which indicated a dihedral angle of around 60°. Thus, it was proposed that the bulky aryl group of 148 was located on the α-face. Also, no phosphine ligand was required, and the reaction conditions were mild.

With the coupled product 125 in hand, reduction of the alkene moiety was carried out. It should be noticed that the reduction product 149 and 150 were inseparable by column chromatography and were subjected to acid hydrolysis as a mixture. Results of the two transformations are summarized in Table 5.

Figure 2:
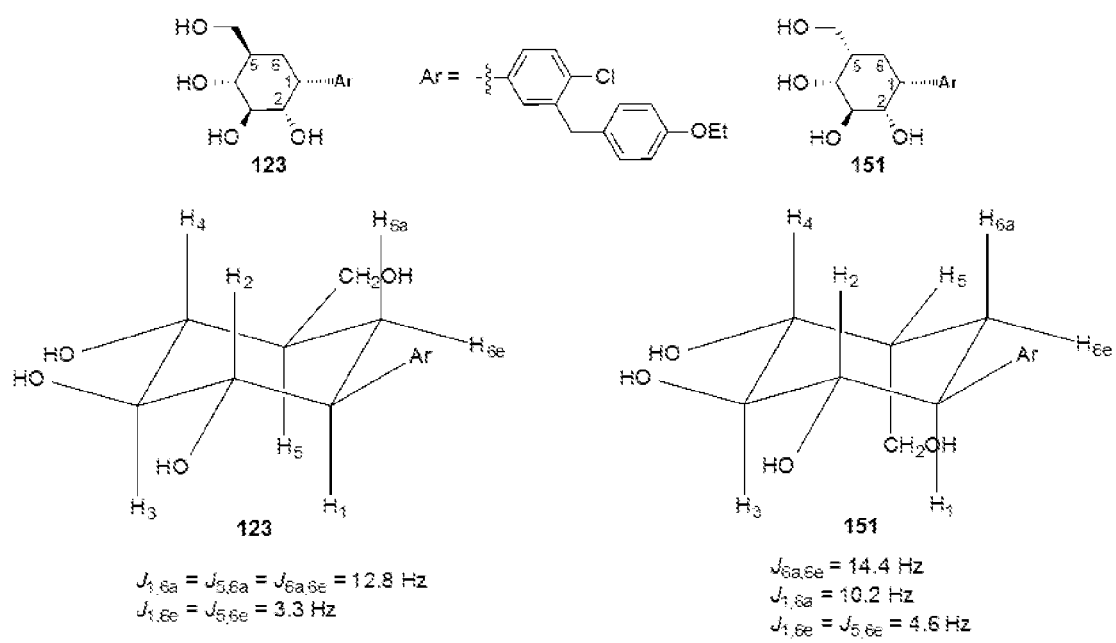
FIG. 2 shows the proposed chair conformations of cyclohexane 123 and 151.

From our experience in performing hydrogenation of some carbocyclic analogues of dapagliflozin, the use of Pd-, Pt- or Ni-based catalysts would lead to extensive dechlorination of the aglycon (to be discussed in the next section). Thus, we first performed the hydrogenation using Ru/C and Rh/C instead of the common heterogeneous catalysts (entries 1 and 2, Table 5). It was then found that both Ru/C and Rh/C were not effective for this transformation, and so diimide reduction was performed (entry 3, Table 5). To our delight, the reduction products were obtained in 82% yield using diimide reduction. Acid hydrolysis followed by preparative TLC gave our target molecule 123 and its C-5 epimer 151 in 9% and 62% yield respectively. The chair conformations of cyclohexane 123 and 151 are proposed in FIG. 2. The proposed structures are inferred from coupling constant analysis.

In summary, the synthetic pathway towards aryl pseudo-C-glycoside 123 consisted of only 9 synthetic manipulations (from D-gluconolactone). A novel Suzuki-type allyl-aryl coupling reaction was applied to establish the key C—C bond. Our synthesis had several advantages over Ohtake's synthesis of a structurally similar aryl pseudo-C-glycoside.[20] First, the convergent synthetic approach significantly reduced the number of organic transformations. Second, the handling of air-sensitive organolithium or organomagnesium reagents was not necessary. Third, the presence of moisture was tolerated in the key C—C bond forming step, which eased the preparation of advanced intermediates.

B. Suzuki-Type Aryl-Allyl Cross Coupling Reaction Between Aryl Boronic Acid 88 and Cyclic Allylic Carbonate 81

After the preparation of both cyclic allylic carbonate 81 and aryl boronic acid 88, the Suzuki-type aryl-ally cross coupling reaction was attempted. Various palladium source and ligands were screened for the coupling reaction and the results are listed in Table 6.

At the beginning, $Pd(OAc)_2$, $Pd(dba)_2$ and Pd/C three palladium source were screen for the coupling reaction. They were applied on a ligand-free condition with $K_2CO_3$ as additive in 1,4-dioxane. The coupling reaction was found to be stereospecific. Pd/C was found to give the cyclohexene 116 in poor yield with significant amount of the elimination product, diene 117. $Pd(OAc)_2$ showed an improved result, which gave cyclohexene 116 in fair yield, but again with significant amount of diene 117. (Entries 1 and 2, Table 6) While $Pd(dba)_2$ gave the cyclohexene 116 in very good yield together with small amount of the side product, diene 117. (Entry 3, Table 6)

Subsequently, $Pd(dba)_2$ was selected as the palladium source for the screening. Several bidentate phosphine base ligands were screen to optimize the coupling reaction. Surprisingly, the ligand-free condition gave the best yield when compared to the conditions with ligands. Using dppf, dppp or dppe as ligands for the coupling reaction only gave cyclohexene 116 in low yield and promoted the formation of the elimination side product diene 117 (Entry 4-6, Table 6). Thereafter, ligand-free $Pd(dba)_2$ condition was chosen for further screening of reaction optimization. Different additives, solvents and temperature were screened and the results are listed in Table 7.

Besides the ligand-free $Pd(dba)_2$ with $K_2CO_3$ condition (Entry 1, Table 7), different additives were screened. Potassium fluoride, which was reported to promote Suzuki-coupling due to the formation of reactive fluoroborate, and potassium phosphate tribasic trihydrate, which was another common additive for Suzuki coupling reaction, were used as additive.[21] Although both salt gave good yield of cyclohexene 116 and a small amount of elimination product, diene 117, but they were still not better than the potassium carbonate. (Entries 2 and 3, Table 7)

Therefore, different carbonate sources were screened for the coupling reaction. Conditions with sodium carbonate and cesium carbonate as additives were attempted. Both salt resulted in good yield of cyclohexene 116 with small amount of elimination product, diene 117. (Entry 4 and 5, Table 7) But again, potassium carbonate gave a batter result then these salts.

Thereafter, solvents for the reaction were screened. In addition to 1,4-dioxane, THF was also used as a polar solvent for the reaction and gave cyclohexene 116 in good yield. (Entry 6, Table 7). Besides polar solvent, relatively non-polar solvent like $CH_2Cl_2$, $CHCl_3$ and toluene were used as well. However, these solvents gave cyclohexene 116 in poor yield with significant amount of elimination product, diene 117, in near one to one ratio. (Entries 7-9, Table 7) Another polar solvent, $CH_3CN$, was used for the coupling reaction as well. However, aryl boronic acid 88 was only slightly soluble in $CH_3CN$. The reaction took longer time to complete and only gave low yield of cyclohexene 116 with large amount of elimination product, diene 117. (Entry 10, Table 7) The reaction was also carried out at raised temperature to speed up the reaction. Nevertheless, reaction at 50° C. only gave poor yield of cyclohexene 116 and promoted the formation of elimination product, diene 117. (Entry 11, Table 7) Eventually, the optimized condition is using ligand-free $Pd(dba)_2$ as palladium source with potassium carbonate as additive in 1,4-dioxane. Cyclohexene 116 was obtained from cyclic allylic carbonate 81 and aryl boronic acid 88 through a stereo- and regioselective Suzuki-type aryl-allyl cross coupling reaction. (Scheme 9)

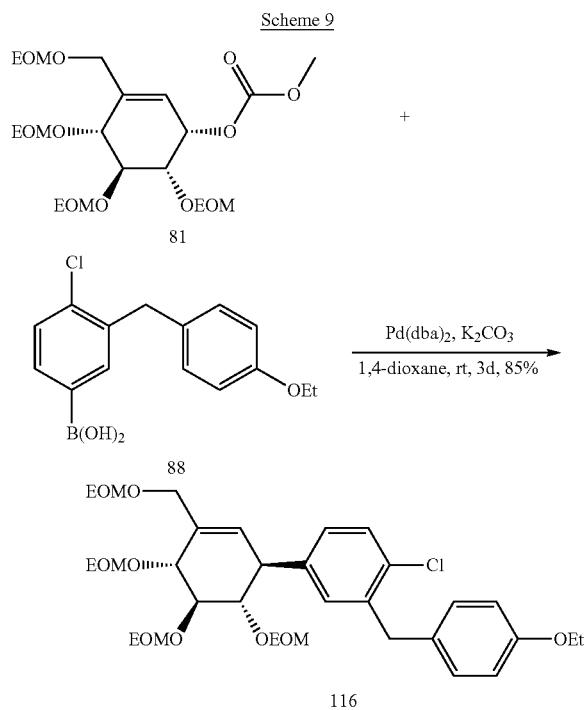

IV. Preparation of Carbocyclic-Alkene Analogue of Dapagliflozin

Besides target compound 80, the carbocyclic-alkene analogue of dapagliflozin (14), tetraol 118 was also explored as it due to its potential to provide additional information on the SAR study. Tetraol 118 was easily obtained from global deprotection of cyclohexene 116 by heating with aqueous hydrochloric acid in EtOH. (Scheme 10)

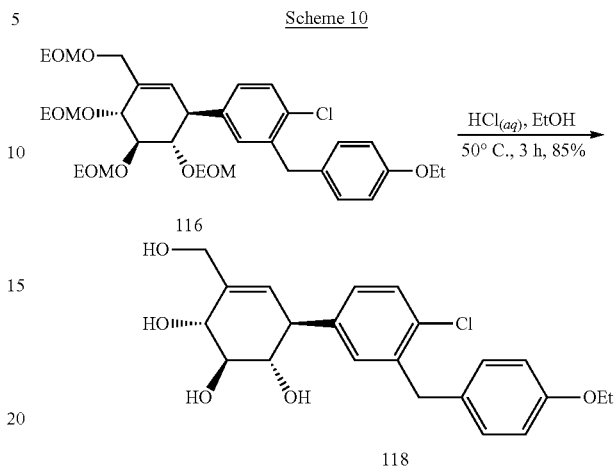

V. Olefin Reduction of Cyclohexene 116

With cyclohexene 116 in hand, the next step was to reduce the olefin into saturated carbon-carbon bond. A common method is transition metal catalyzed hydrogenation. Platinum, palladium, rhodium, ruthenium and nickel were generally used to catalyze hydrogenation of olefin by gaseous hydrogen.[22] However, there were number of reports indicated that hydrogenolysis of C—Cl bond might occur on aryl chloride under hydrogen atmosphere in the presence of transition metal catalysts.[23-26] According to Washburn's SAR study on the aglycone moiety, the chlorine atom on the C4' position of the diarylmethane serve as a lipophilic group and it was important as it increase the SGLT2 affinity; so the chlorine atom should not be removed.[27] Hence, a model reaction was first carried out on the aglycone, diarylmethane 40, to see whether hydrogenolysis would occur on our substrate.

VI. Hydrogenation Model Reactions for the Study of Hydrogenolysis on Aryl Chloride Various hydrogenation conditions were explored using the commercial available diarylmethane 40 for the study of hydrogenolysis. The results are listed in Table 8.

Different transition metal catalysts were used to mimic the hydrogenation condition. All the Pt- Pd- and Ni-based catalysts resulted in dechlorination to give diarylmethane 120 in excellent yield and no chlorinated-diarylmethane 119 was observed. Therefore, the Pt- Pd- and Ni-based catalysts might not be suitable catalysts for the olefin reduction.

Next, a series of hydrogenation reaction were attempted by using Rh/C or Ru/C as catalysts for the reduction of cyclohexene 116 and the results are listed in Table 9. For both Rh/C and Ru/C catalysts, hydrogenation were attempted by using MeOH, EtOH, iPrOH, tBuOH and 1,4-dioxane as solvents. However, all trials resulted in no reaction. Rh/C and Ru/C were found to be not effective in this hydrogenation. (Entry 1-10, Table 9)

Thereafter, several diimide reductions were attempted to reduce cyclohexene 116 and the results are listed in Table 10. The diimide reduction was first carried out according to the reported method.[28,29] Cyclohexene 116 was dissolved in a solution of $THF/H_2O$ mixture and warmed at 70° C. NaOAc and $pTsNHNH_2$ were added in 4 hours intervals. The reaction yielded cyclohexanes 121 and 122, which were an inseparable mixture, in total of 82% after 5 days. (Entry 1, Table 10) Reaction at higher temperature was attempted to try to shorten the time required for completing the reaction. Out of expectation, reaction at 90° C. required double reaction time, i.e. 10 days, and gave similar yield as the reaction carried out at 70° C. (Entry 2, Table 10) Reaction was then carried out at lower temperature, the trial at 50° C., however, did not give any reaction. (Entry 3, Table 10) A trial using pure THF as solvent was also attempted. The reaction was carried out at 70° C. and took 7 days to complete. The yield slight dropped to 74% (Entry 4, Table 10) It was reported that diimide would decompose rapidly at room temperature such that the half-life was just several minutes.[30] The in situ generated diimide at elevated temperature could decompose even at a faster rate thus the 4 hours interval would be too long and could not provide continuous supply of diimide for the reduction of cyclohexene 116. Another trial at 70° C. was carried out and the diimide precursor, pTsNHNH$_2$, was added every 5 minutes. The reaction was completed in 4.5 h and gave cyclohexanes 121 and 122 in a total of 83% yield, which was similar to that of entry 1 and 2 of table 7. (Entry 5, Table 10) Therefore, cyclohexene 116 was reduced to an inseparable mixture of cyclohexanes 121 and 122 by diimide reduction in very good yield. (Scheme 11)

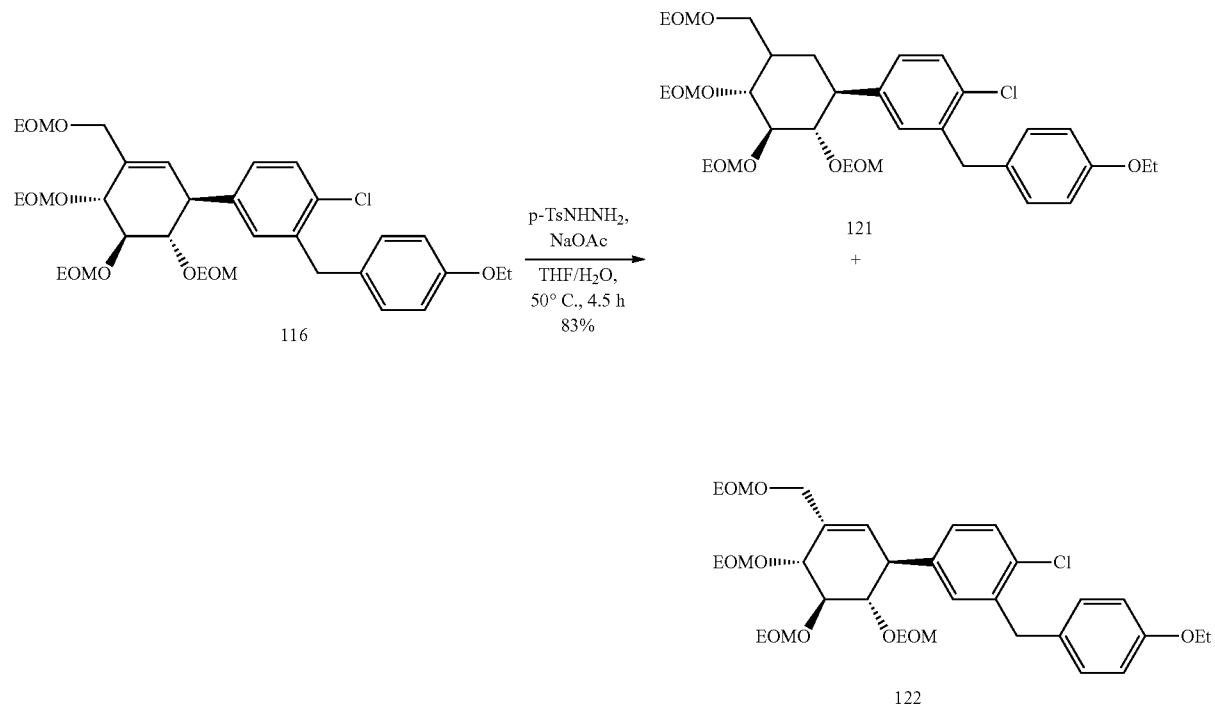

VII. Global Deprotection of Cyclohexanes 121 and 122

Cyclohexanes 121 and 122 were found to be an inseparable mixture. Their similar polarity made them difficult to be separated by column chromatography. Global deprotection of mixture 121 and 122 by aqueous hydrochloric acid in EtOH yield our target, tetraol 80 and the corresponding C5 epimer, tetraol 130. (Scheme 12)

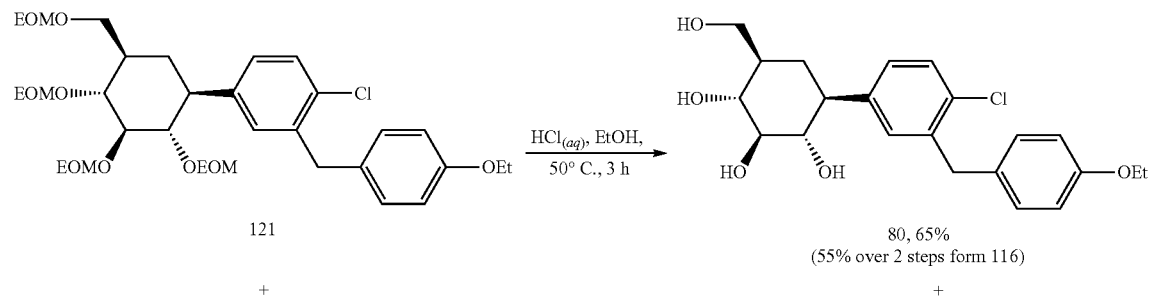

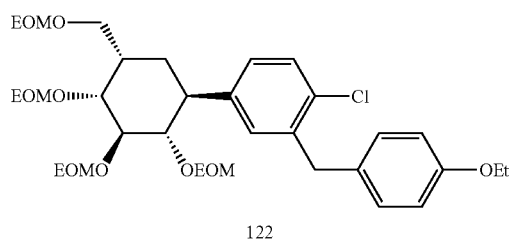

122

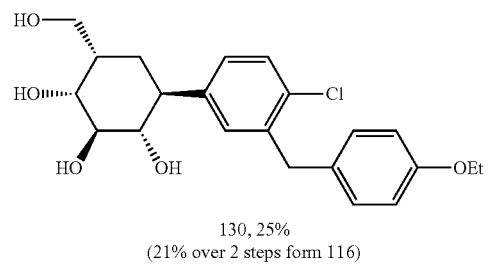

130, 25%
(21% over 2 steps form 116)

The two epimers were separated by preparative TLC under CHCl$_3$/MeOH solvent system to give pure tetraols 80 and 130.

VIII. Characterization of Tetraol 80

The stereochemistry of tetraol 80 is in vital importance to the inhibition towards SGLT2. The carbasugar should mimic the structure of β-D-glucopyranoside to achieve the best potency. $^1$H, $^{13}$C, COSY and HMQC NMR spectroscopies were done on tetraol 80 to verify the stereochemistry and the data are listed in Table 11. By the HMQC results, H$_1$, H$_5$, H$_{6a}$ and H$_{6e}$ could be easily identified in the $^1$H NMR spectrum. It was found that H$_{6a}$ showed a quartet with coupling constant at around 13 Hz. With the aid of COSY results, H$_{6a}$ was found to be coupling with three other protons, H$_1$, H$_5$ as well as H$_{6e}$. The results indicated that H$_{6a}$ is coupling with these three protons in germinal or di-axial manner and thus verify the stereochemistry at C1 and C5 position.

Figure 3:
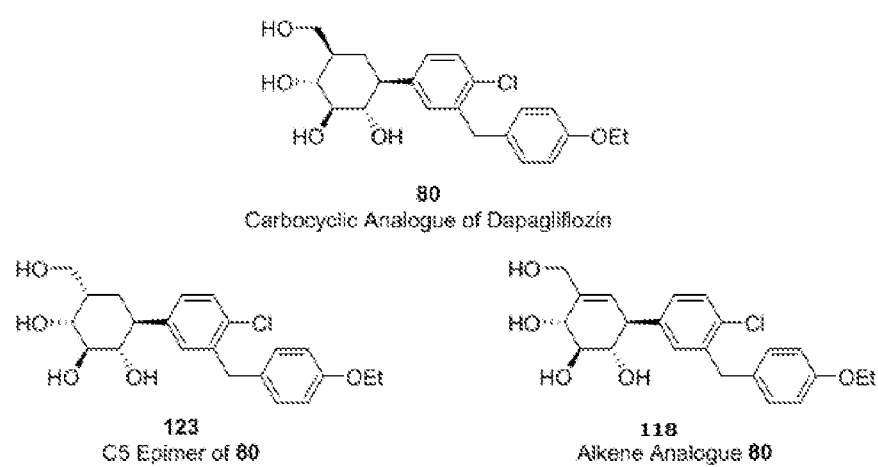
FIG. 3 shows the chemical structure of tetraol 80, which was the carbocyclic analogue of dapagliflozin (14), the corresponding C5 epimer, tetraol 130, and an alkene analogue, tetraol 118.

IX. Aryl-C-5-Carba-Glycosides Prepared for $^{14}$C-α-Methyl-D-glucopyranoside ($^{14}$C-AMG) Uptake Assay In addition to the synthetic target tetraol 80, which was the carbocyclic analogue of dapagliflozin (14), the corresponding C5 epimer, tetraol 130, and an alkene analogue, tetraol 118, were also prepared. (FIG. 3) These compounds were sent for the $^{14}$C-α-methyl-D-glucopyranoside ($^{14}$C-AMG) uptake assay to investigate the inhibitory and selectivity performance towards SGLT2 and SGLT1. The SAR could be study according to the difference of the results.

With the novel mechanism and outstanding potency, SGLT2 inhibitors would be the first-line drug treatment of type 2 diabetes mellitus in the coming generation. SGLT2 inhibitors with good potency and selectivity as well as improved metabolic stability are in interested. Inspired by the marketed Dapagliflozin (14), a series of aryl-C-5-carba-glycosides, which were the carbocyclic analogues of Dapagliflozin, were designed and synthesized. Starting from commercially available D-gluconolactone (38), the carbasugar glycone, cyclic α-allylic alcohol 86, was prepared by a carbocyclization strategy with 5 steps in 53% yield. The coupling partner, cyclic allylic carbonate 81, was prepared from cyclic α-allylic alcohol 86 in 74% yield (BORSM 92%). The glycone, cyclic α-allylic alcohol 86, and the aglycone, aryl boronic acid 88, were coupled through a Suzuki-type allyl-aryl cross coupling reaction to give cyclohexene 116 in 85% yield. Followed by olefin reduction and global deprotection, the target aryl-C-5-carba-glycoside, tetraol 80, was prepared in 55% over two steps. (Scheme 13) As a result, target aryl-C-5-carba-glycoside, tetraol 80, was transformed from D-gluconolactone (38) through 9 steps in overall 18% yield. The corresponding C5 epimer, tetraol 130, and an alkene analogue, tetraol 118, of tetraol 80 were also prepared.

Scheme 13

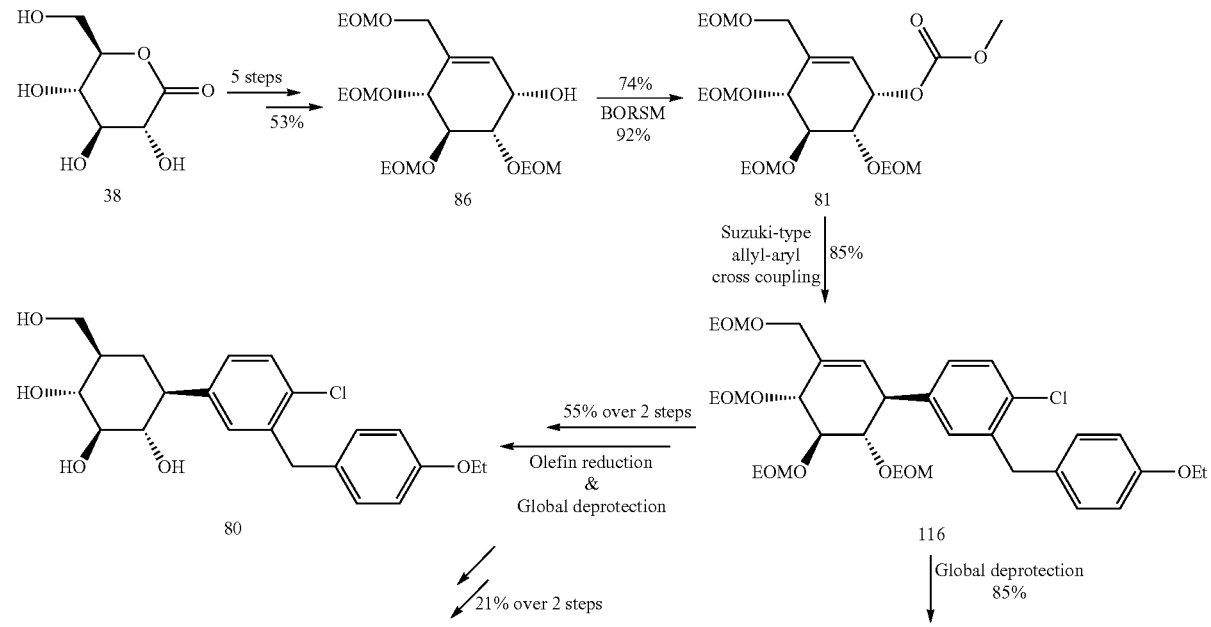

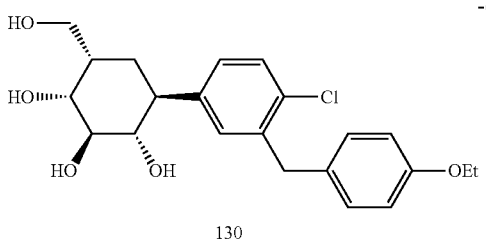

130

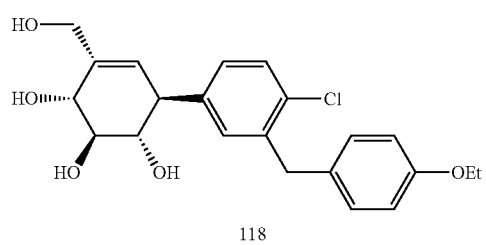

118

X. Treatment of Diabetes and Related Conditions

By demonstrating that the aryl pseudo-C-glycoside compounds of this invention are effective modulators of sugar metabolism capable of alleviating, eliminating, or reversing the symptoms or effects of diabetes and other related conditions such as pre-diabetic high blood glucose, metabolic syndrome, the present inventors have established that these novel aryl pseudo-C-glycoside compounds are useful for medical intervention both therapeutically and prophylactically. These compounds are therefore useful therapeutic agents for treating patients who have been diagnosed or are at risk of developing diseases or conditions where improper sugar metabolism is present.

A. Pharmaceutical Compositions

Compounds of the present invention are useful in the manufacture of a pharmaceutical composition or a medicament. A pharmaceutical composition or medicament can be administered to a subject for the treatment of a metabolic disease such as diabetes.

The aryl pseudo-C-glycoside compounds of the present invention are suitable in the manufacture of a pharmaceutical composition or a medicament comprising an effective amount thereof in conjunction or mixture with excipients or carriers suitable for application.

An exemplary pharmaceutical composition of this invention comprises (i) one or more aryl pseudo-C-glycoside compounds as described herein, and (ii) a pharmaceutically acceptable excipient or carrier. The terms pharmaceutically-acceptable and physiologically-acceptable are used synonymously herein. The aryl pseudo-C-glycoside compound(s) may be provided in a therapeutically effective dose for use in a method for treatment as described herein.

The pharmaceutical compositions of the carriers include but are not limited to: liposomes, nanoparticles, vesicles, microbubbles, microspheres, nano-bubbles, micelles, emulsions, gels, liquid crystals, biomedical materials, etc. The compositions can be composed of general delivery vehicles or accessories, including but not limited to ethyl alcohol, polyethylene glycol, dimethylsulfoxide, Tween, glycerol, castor oil, buffers, etc.

An aryl pseudo-C-glycoside compound of this invention can be administered via liposomes, which serve to target the conjugates to a particular tissue, as well as increase the half-life of the composition. Liposomes include emulsions, foams, micelles, insoluble monolayers, liquid crystals, phospholipid dispersions, lamellar layers and the like. In these preparations the compound to be delivered is incorporated as part of a liposome, alone or in conjunction with a molecule which binds to, e.g., a receptor prevalent among the targeted cells or tissues (e.g., epithelial cells), or with other therapeutic or immunogenic compositions. Thus, liposomes filled with an aryl pseudo-C-glycoside compound of the invention can be directed to the site of treatment, where the liposomes then deliver the composition. Liposomes for use in the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka et al. (1980) Ann. Rev. Biophys. Bioeng. 9: 467, U.S. Pat. Nos. 4,235,871, 4,501,728 and 4,837,028.

Pharmaceutical compositions or medicaments for use in the present invention can be formulated by standard techniques using one or more physiologically acceptable carriers or excipients. Suitable pharmaceutical carriers are described herein and in "Remington's Pharmaceutical Sciences" by E. W. Martin. The aryl pseudo-C-glycoside compounds of the present invention and their physiologically acceptable salts and solvates can be formulated for administration by any suitable route, including via inhalation, topically, nasally, orally, parenterally, or rectally.

Typical formulations for topical administration include creams, ointments, sprays, lotions, and patches. The pharmaceutical composition can, however, be formulated for any type of administration, e.g., intradermal, subdermal, intravenous, intramuscular, intranasal, intracerebral, intratracheal, intraarterial, intraperitoneal, intravesical, intrapleural, intracoronary or intratumoral injection, with a syringe or other devices. Formulation for administration by inhalation (e.g., aerosol), or for oral, rectal, or vaginal administration is also contemplated.

B. Routes of Administration

Suitable formulations for topical application, e.g., to the skin and eyes, are preferably aqueous solutions, ointments, creams or gels well-known in the art. These formulations may contain solubilizers, stabilizers, tonicity enhancing agents, buffers and/or preservatives.

Suitable formulations for transdermal application include an effective amount of an aryl pseudo-C-glycoside compound of the present invention with carrier. Preferred carriers include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used.

For oral administration, a pharmaceutical composition or a medicament can take the form of, for example, a tablet or a capsule prepared by conventional means with a pharmaceutically acceptable excipient. Preferred are tablets and gelatin capsules comprising the active ingredient, i.e., an aryl pseudo-C-glycoside compound, together with (a) diluents or fillers, e.g., lactose, dextrose, sucrose, mannitol, sorbitol, cellulose (e.g., ethyl cellulose, microcrystalline cellulose), glycine, pectin, polyacrylates and/or calcium hydrogen phosphate, calcium sulfate, (b) lubricants, e.g., silica, talcum, stearic acid, its magnesium or calcium salt, metallic stearates, colloidal silicon dioxide, hydrogenated vegetable oil, corn starch, sodium benzoate, sodium acetate and/or polyethyleneglycol; for tablets also (c) binders, e.g., magnesium aluminum silicate, starch paste, gelatin, tragacanth, methylcellulose, sodium carboxymethylcellulose, polyvinylpyrrolidone and/or hydroxypropyl methylcellulose; if desired (d) disintegrants, e.g., starches (e.g., potato starch or sodium starch), glycolate, agar, alginic acid or its sodium salt, or effervescent mixtures; (e) wetting agents, e.g., sodium lauryl sulphate, and/or (f) absorbents, colorants, flavors and sweeteners.

Tablets may be either film coated or enteric coated according to methods known in the art. Liquid preparations for oral administration can take the form of, for example, solutions, syrups, or suspensions, or they can be presented as a dry product for constitution with water or other suitable vehicle before use. Such liquid preparations can be prepared by conventional means with pharmaceutically acceptable additives, for example, suspending agents, for example, sorbitol syrup, cellulose derivatives, or hydrogenated edible fats; emulsifying agents, for example, lecithin or acacia; non-aqueous vehicles, for example, almond oil, oily esters, ethyl alcohol, or fractionated vegetable oils; and preservatives, for example, methyl or propyl-p-hydroxybenzoates or sorbic acid. The preparations can also contain buffer salts, flavoring, coloring, and/or sweetening agents as appropriate. If desired, preparations for oral administration can be suitably formulated to give controlled release of the aryl pseudo-C-glycoside compound of this invention.

The aryl pseudo-C-glycoside compounds of the present invention can be formulated for parenteral administration by injection, for example by bolus injection or continuous infusion. Formulations for injection can be presented in unit dosage form, for example, in ampoules or in multi-dose containers, with an added preservative. Injectable compositions are preferably aqueous isotonic solutions or suspensions, and suppositories are preferably prepared from fatty emulsions or suspensions. The compositions may be sterilized and/or contain adjuvants, such as preserving, stabilizing, wetting or emulsifying agents, solution promoters, salts for regulating the osmotic pressure and/or buffers. Alternatively, the active ingredient can be in powder form for constitution with a suitable vehicle, for example, sterile pyrogen-free water, before use. In addition, they may also contain other therapeutically valuable substances. The compositions are prepared according to conventional mixing, granulating or coating methods, respectively, and contain about 0.1 to 75%, preferably about 1 to 50%, of the active ingredient.

For administration by inhalation, the active ingredient, e.g., an aryl pseudo-C-glycoside compound of this invention, may be conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide, or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the compound and a suitable powder base, for example, lactose or starch.

The aryl pseudo-C-glycoside compounds can also be formulated in rectal compositions, for example, suppositories or retention enemas, for example, containing conventional suppository bases, for example, cocoa butter or other glycerides.

Furthermore, the aryl pseudo-C-glycoside compounds can be formulated as a depot preparation. Such long-acting formulations can be administered by implantation (for example, subcutaneously or intramuscularly) or by intramuscular injection. Thus, for example, the aryl pseudo-C-glycoside compounds can be formulated with suitable polymeric or hydrophobic materials (for example as an emulsion in an acceptable oil) or ion exchange resins, or as sparingly soluble derivatives, for example, as a sparingly soluble salt.

A pharmaceutical composition or medicament of the present invention comprises (i) an effective amount of an aryl pseudo-C-glycoside compound as described herein that acts as a modulator of sugar metabolism, and (ii) another therapeutic agent. When used with a compound of the present invention, such therapeutic agent may be used individually, sequentially, or in combination with one or more other such therapeutic agents (e.g., a first therapeutic agent, a second therapeutic agent, and an aryl pseudo-C-glycoside compound of the present invention). Administration may be by the same or different route of administration or together in the same pharmaceutical formulation.

C. Dosage

Pharmaceutical compositions or medicaments can be administered to a subject at a therapeutically effective dose to prevent, treat, or control a metabolic disorder (e.g., diabetes) as described herein. The pharmaceutical composition or medicament is administered to a subject in an amount sufficient to elicit an effective therapeutic response in the subject.

The dosage of active agents administered is dependent on the subject's body weight, age, individual condition, surface area or volume of the area to be treated and on the form of administration. The size of the dose also will be determined by the existence, nature, and extent of any adverse effects that accompany the administration of a particular compound in a particular subject. For example, each individual compound of the aryl pseudo-C-glycoside compounds described herein may have a unique dosage. A unit dosage for oral administration to a mammal of about 50 to 70 kg may contain between about 5 and 500 mg of the compound. Typically, a dosage of the aryl pseudo-C-glycoside compound of the present invention is a dosage that is sufficient to achieve the desired effect. Optimal dosing schedules can be calculated from measurements of agent accumulation in the body of a subject. In general, dosage may be given once or more daily, weekly, or monthly. Persons of ordinary skill in the art can easily determine optimum dosages, dosing methodologies and repetition rates.

To achieve the desired therapeutic effect, the aryl pseudo-C-glycoside compounds may be administered for multiple days at the therapeutically effective daily dose. Thus, therapeutically effective administration of the compounds to treat a pertinent condition or disease described herein in a subject requires periodic (e.g., daily) administration that continues for a period ranging from three days to two weeks or longer. Typically, the aryl pseudo-C-glycoside compounds will be administered for at least three consecutive days, often for at least five consecutive days, more often for at least ten, and sometimes for 20, 30, 40 or more consecutive days. While consecutive daily doses are a preferred route to achieve a therapeutically effective dose, a therapeutically beneficial effect can be achieved even if the compounds are not administered daily, so long as the administration is repeated frequently enough to maintain a therapeutically effective concentration of the compounds in the subject. For example, one can administer the agents every other day, every third day, or, if higher dose ranges are employed and tolerated by the subject, once a week.

Optimum dosages, toxicity, and therapeutic efficacy of the compounds may vary depending on the relative potency of individual compounds and can be determined by standard pharmaceutical procedures in cell cultures or experimental animals, for example, by determining the $LD_{50}$ (the dose lethal to 50% of the population) and the $ED_{50}$ (the dose therapeutically effective in 50% of the population). The dose ratio between toxic and therapeutic effects is the therapeutic index and can be expressed as the ratio, $LD_{50}/ED_{50}$. Particular compounds that exhibit large therapeutic indices are preferred. While compounds that exhibit toxic side effects can be used, care should be taken to design a delivery system that targets such compounds to the site of affected tissue to minimize potential damage to normal cells and thereby reduce side effects.

The data obtained from, for example, cell culture assays and animal studies can be used to formulate a dosage range for use in humans. The dosage of such compounds lies preferably within a range of circulating concentrations that include the $ED_{50}$ with little or no toxicity. The dosage can vary within this range depending upon the dosage form employed and the route of administration. For any compounds used in the methods of the invention, the therapeutically effective dose can be estimated initially from cell culture assays. A dose can be formulated in animal models to achieve a circulating plasma concentration range that includes the $IC_{50}$ (the concentration of the compound that achieves a half-maximal inhibition of symptoms) as determined in cell culture. Such information can be used to more accurately determine useful doses in humans. Levels in plasma can be measured, for example, by high performance liquid chromatography (HPLC). In general, the dose equivalent of compounds is from about 1 ng/kg to 100 mg/kg for a typical subject.

Exemplary dosages for an aryl pseudo-C-glycoside compound described herein are provided. Dosage for an aryl pseudo-C-glycoside compound can be between 0.1-0.5 mg/dose, with systemic administration (e.g., 5-30 mg/kg body weight). The compounds can be administered orally at between 5-1000 mg, or by intravenous infusion at between 10-500 mg/ml. In the alternative, the compounds can be administered by intravenous injection or infusion at 50-500 mg/ml (over 120 minutes); 1-500 mg/kg (over 60 minutes); or 1-100 mg/kg (bolus) five times weekly. The aryl pseudo-C-glycoside compounds can be administered subcutaneously at 10-500 mg; 0.1-500 mg/kg intravenously twice daily, or about 50 mg once weekly, or 25 mg twice weekly.

Pharmaceutical compositions of the present invention can be administered alone or in combination with at least one additional therapeutic compound. Exemplary advantageous therapeutic compounds include systemic and topical anti-inflammatories, pain relievers, anti-histamines, anesthetic compounds, antibiotics, and the like. The additional therapeutic compound can be administered at the same time as, or even in the same composition with, main active ingredient (e.g., an aryl pseudo-C-glycoside compound of this invention). The additional therapeutic compound can also be administered separately, in a separate composition, or a different dosage form from the main active ingredient. Some doses of the main ingredient, such as a novel aryl pseudo-C-glycoside compound described herein, can be administered at the same time as the additional therapeutic compound, while others are administered separately, depending on the particular symptoms and characteristics of the individual.

The dosage of a pharmaceutical composition of the present invention can be adjusted throughout treatment, depending on severity of symptoms, frequency of recurrence, and physiological response to the therapeutic regimen. Those of skill in the art commonly engage in such adjustments in therapeutic regimen.

XI. Kits

In addition to pharmaceutical compositions, the invention provides kits for practicing the methods described herein for treating a metabolic disorder in a subject, such as diabetes, prediabetic high blood glucose, and metabolic syndrome. For example, the kits may contain a collection of separate containers, each containing a single dose of a pharmaceutical composition comprising an aryl pseudo-C-glycoside compound of this invention suitable to act as a sugar metabolism modulator for a therapeutic or prophylactic regimen intended for a metabolic disorder (e.g., diabetes), where abnormal sugar metabolism may play a role. Frequently, the kits further contain instructional material providing description for a user to administer the pharmaceutical composition comprising the aryl pseudo-C-glycoside compound of this invention.

EXAMPLES

The following examples are provided by way of illustration only and not by way of limitation. Those of skill in the art will readily recognize a variety of non-critical parameters that could be changed or modified to yield essentially the same or similar results.

Example 1

Boronic Acid 124

To a solution of aryl bromide 143 (1.50 g, 4.62 mmol) in dry THF (6.2 mL) and dry toluene (24.6 mL) was added dropwise n-butyllithium in n-hexane (1.6 M solution, 5.2 mL, 8.32 mmol) at −78° C. under $N_2$. The reaction mixture was stirred for 30 min at −78° C. under $N_2$. To this mixture was added triisopropyl borate (1.7 mL, 7.39 mmol) at −78° C. under $N_2$. The temperature of the mixture was allowed to increase to −20° C. over 2 h. To this mixture was added 1M HCl (aq) (30 mL) at −20° C., and the mixture was stirred at 0° C. for 1 h. The aqueous phase was extracted with EtOAc (4×30 mL) and the combined organic extracts were washed with brine, dried over anhydrous $MgSO_4$, and filtered. Concentration of the filtrate followed by flash chromatography (hexane:EtOAc, 2.5:1) yielded aryl boronic acid 124 (684 mg, 51%) as a white solid.

Example 2

Boronic Ester 147

To a solution of aryl boronic acid 124 (81.9 mg, 0.282 mmol) in toluene (3 mL) was added pinacol (133 mg, 1.13 mmol). The mixture was heated to reflux with Dean and Stark apparatus for 7 h. The mixture was then cooled down to room temperature and concentrated under reduced pressure. The residue was purified by flash chromatography (hexane:EtOAc, 20:1) to afford boronic ester 147 (96.2 mg, 92%) as a colorless oil: $R_f$ 0.43 (hexane:EtOAc, 20:1); IR (thin film) 2978, 2920, 2850, 1598, 1510, 1395, 1358, 1269, 1244, 1144, 1096, 1045, 965, 853, 825 $cm^{-1}$; $^1H$ NMR (400 MHz, $CDCl_3$) δ 1.35 (12H, s), 1.40 (3H, t, J=6.9 Hz), 4.00 (2H, q, J=6.9 Hz), 4.07 (2H, s), 6.81 (2H, d, J=8.4 Hz), 7.11 (2H, d, J=8.2 Hz), 7.38 (1H, d, J=7.9 Hz), 7.61 (1H, d, J=7.8 Hz), 7.71 (1H, s); $^{13}C$ NMR (100 MHz, $CDCl_3$) δ 15.0 ($CH_3$), 15.1 ($CH_3$), 15.2 ($CH_3$), 15.3 ($CH_3$), 27.9 ($CH_2$), 29.9 ($CH_2$), 35.6 (CH), 38.7 ($CH_2$), 63.5 ($CH_2$), 63.5 ($CH_2$), 63.7 (CH$_2$), 63.9 (CH$_2$), 64.0 (CH$_2$), 66.6 (CH$_2$), 75.6 (CH), 78.3 (CH), 78.7 (CH), 79.7 (CH), 95.4 (CH$_2$), 95.6 (CH$_2$), 96.3 (CH$_2$), 96.5 (CH$_2$), 114.5 (CH), 114.6 (CH), 118.8 (CH), 125.7 (C), 130.0 (CH), 130.2 (CH), 131.4 (C), 140.3 (C), 156.9 (C), 157.6 (C); $^{11}$B NMR (128 MHz) δ 30.6 (br s); MS (ESI) m/z (relative intensity) 395 ([M+Na]$^+$, 100); HRMS (ESI) calcd for C$_{21}$H$_{26}$BClO$_3$ [M+Na]$^+$ 395.1559, found 395.1554.

Example 3

Allylic Chloride 60

To a solution of α-allyic alcohol 52 (377 mg, 0.92 mmol) and tetra-n-butylammonium chloride (1.28 g, 4.61 mmol) in CH$_2$Cl$_2$ (9 mL) was added Et$_3$N (0.39 mL, 2.77 mmol). Then 3 Å molecular sieves (ca. 1.0 g) was added and the mixture was stirred for 15 min. Methanesulfonyl chloride (MsCl) (0.14 mL, 1.84 mmol) was then added at 0° C. and the solution was stirred for 15 min at 0° C. After stirred for 3 h at room temperature, the reaction mixture was then quenched with saturated NaHCO$_3$ solution (20 mL). The aqueous phase was extracted with EtOAc (3×25 mL) and the combined organic extracts were washed with brine, dried over anhydrous MgSO$_4$, and filtered. Concentration of the filtrate followed by flash chromatography (hexane:EtOAc, 6:1) yielded allylic chloride 60 (319 mg, 81%) as a colorless oil: [α]$_D^{20}$ −84.3 (c 1.72, CHCl$_3$); R$_f$ 0.23 (hexane:EtOAc, 6:1); IR (thin film) 2976, 2932, 2886, 1483, 1470, 1455, 1445, 1391, 1182, 1115, 1110, 1047, 1018, 847, 767 cm$^{-1}$; $^1$H NMR (400 MHz, CHCl$_3$) δ 1.19-1.24 (12H, m), 3.53-3.67 (6H, m), 3.69-3.80 (2H, m), 3.81-3.89 (2H, m), 4.11-4.18 (2H, m), 4.23 (1H, d, J=7.1 Hz), 4.54 (1H, dt, J=7.1, 2.3 Hz), 4.70 (2H, s), 4.77 (1H, d, J=6.7 Hz), 4.84-4.94 (5H, m), 5.79 (1H, s); $^{13}$C NMR (100 MHz, CHCl$_3$) δ 15.1 (CH$_3$), 15.2 (CH$_3$), 15.3 (CH$_3$), 15.3 (CH$_3$), 59.4 (CH), 63.6 (CH$_2$), 64.3 (CH$_2$), 64.5 (CH$_2$), 64.6 (CH$_2$), 66.4 (CH$_2$), 80.6 (CH), 80.6 (CH), 94.8 (CH$_2$), 96.3 (CH$_2$), 96.7 (CH$_2$), 97.1 (CH$_2$), 123.9 (CH), 137.1 (C); MS (ESI) m/z (relative intensity) 449 ([M+Na]$^+$, 100); HRMS (ESI) calcd for C$_{19}$H$_{35}$O$_8$Cl [M+Na]$^+$ 449.1913, found 449.1912.

Example 4

Diol 84

To a stirred solution of D-gluconolactone 38 (10.04 g, 56.4 mmol) and nBu$_4$NI (2.08 g, 5.64 mmol) in CH$_2$Cl$_2$ (94 mL) was added 2,6-lutidine (58.8 mL, 507 mmol) at rt under nitrogen. The reaction mixture was cooled down to 0° C. and added with ethoxymethyl chloride (47.1 mL, 507 mmol) dropwise over 1 h. After stirring vigorously for 60 h at rt, the reaction mixture was then filtered through a short plug of silica gel and quenched with saturated NaHCO$_3$ (120 mL) The aqueous phase was extracted with CH$_2$Cl$_2$ (3×120 mL). The combined organic extracts were washed with brine, dried over anhydrous MgSO$_4$, and filtered. Concentration of the filtrate under reduced pressured gave crude lactone 82. To a stirred solution of diisopropylamine (23.9 mL, 169.2 mmol) in THF (285 mL) at −78° C. under nitrogen was added nBuLi (1.6M in hexane) (106 mL, 169.2 mmol) dropwise over 15 min. The solution was stirred at −78° C. for 15 min and then added with dimethyl methylphosphonate (18.1 mL, 169.2 mmol) dropwise over 5 min. The solution was stirred at −78° C. for 25 min after the addition. To a stirred solution of crude lactone 82 in THF (285 mL) at −78° C. under nitrogen was added the freshly prepared lithiated dimethyl methylphosphonate solution dropwise over 1 h through a wrapped cannula. After stirring at −78° C. under nitrogen for another 30 min, the reaction mixture was then quenched with saturated NH$_4$Cl (500 mL) and the aqueous phase was extracted with EtOAc (3×500 mL). The combined organic extracts were washed with brine, dried over anhydrous MgSO$_4$, and filtered. Concentration of the filtrate under reduced pressured gave crude lactol 83. To a stirred solution of crude lactol 83 in MeOH (190 mL) at 0° C. was added NaBH$_4$ (6.40 g, 169.2 mmol). After stirring at rt for 1 h, the reaction mixture was then quenched with saturated NH$_4$Cl (150 mL) and the aqueous phase was extracted with EtOAc (6×300 mL). The combined organic extracts were washed with brine, dried over anhydrous MgSO$_4$, and filtered. Concentration of the filtrate under reduced pressured followed by flash chromatography (EtOAc:MeOH, 20:1) yielded diol 84 (27.54 g, 91%) as a colourless oil. R$_f$ 0.27 (EtOAc:MeOH, 20:1); HRMS (ESI) calcd for C$_{21}$H$_{45}$O$_{13}$P [M+Na]$^+$ 559.2490, found 559.2492.

Example 6

Cyclic Enone 85

To a stirred solution of trifluoroacetic anhydride (0.54 mL, 3.80 mmol) in CH$_2$Cl$_2$ (5 mL) at −78° C. under nitrogen was added DMSO (0.59 mL, 7.60 mmol) dropwise. The solution was stirred for 30 min and then added with a solution of diol 84 (510 mg, 0.951 mmol) in CH$_2$Cl$_2$ (5 mL) dropwise over 15 min. After stirring at −78° C. for 3 h under nitrogen, DIPEA (1.3 mL, 7.60 mmol) was added dropwise over 5 min. The reaction was then stirred at −78° C. for 1 h under nitrogen and warmed up to rt. DIPEA (2.0 mL, 11.4 mmol) was added dropwise and the reaction mixture was stirred for another 12 h at rt under nitrogen. The reaction mixture was then quenched with saturated NH$_4$Cl (10 mL) and the aqueous phase was extracted with CH$_2$Cl$_2$ (3×25 mL). The combined organic extracts were washed with brine, dried over anhydrous MgSO$_4$, and filtered. Concentration of the filtrate under reduced pressured followed by flash chromatography (hexane:EtOAc, 4:1) yielded cyclic enone 85 (297 mg, 77%) as a colourless oil. R$_f$ 0.23 (hexane:EtOAc, 4:1); HRMS (ESI) calcd for C$_{19}$H$_{34}$O$_9$ [M+Na]$^+$ 429.2095, found 429.2077.

Example 7

Cyclic α-Allylic Alcohol 86

To a stirred solution of cyclic enone 85 (2.15 g, 5.28 mmol) in THF (55 mL) at −78° C. under nitrogen, superhydride (1M in THF, 16 mL) was added dropwise 30 min. The reaction mixture was stirred at −78° C. for 1 h and then quenched with saturated NH$_4$Cl (50 mL). The aqueous phase was extracted with EtOAc (3×50 mL) and he combined organic extracts were washed with brine, dried over anhydrous MgSO$_4$, and filtered. Concentration of the filtrate under reduced pressured followed by flash chromatography (hexane:EtOAc, 3:2) yielded cyclic cyclic α-allylic alcohol 86 (1.62 g, 75%) as a colourless oil. R$_f$ 0.2 (hexane:EtOAc, 3:2); HRMS (ESI) calcd for C$_{19}$H$_{36}$O$_9$ [M+Na]$^+$ 432.2252, found 431.2252.

Example 8

Cyclic β-Allylic Alcohol 87

To a stirred solution of cyclic enone 85 (2.15 g, 5.28 mmol) in THF (55 mL) at −78° C. under nitrogen, superhydride (1M in THF, 16 mL) was added dropwise 30 min. The reaction mixture was stirred at −78° C. for 1 h and then quenched with saturated NH$_4$Cl (50 mL). The aqueous phase was extracted with EtOAc (3×50 mL) and he combined organic extracts were washed with brine, dried over anhydrous MgSO$_4$, and filtered. Concentration of the filtrate under reduced pressured followed by flash chromatography (hexane:EtOAc, 3:2) yielded cyclic β-allylic alcohol 87 (0.34 g, 16%) as a colourless oil. $R_f$ 0.37 (hexane:EtOAc, 3:2); HRMS (ESI) calcd for $C_{19}H_{36}O_9$ [M+Na]$^+$ 432.2252, found 431.2243.

Example 9

Cyclic Allylic Carbonate 81

To a stirred solution of cyclic α-allylic alcohol 86 (602.1 mg, 1.474 mmol) in pyridine (5 mL) was added methyl chloroformate (0.6 mL) dropwise over 10 min at 0° C. After stirring at rt for 24 h under nitrogen, the reaction mixture was then quenched with saturated NaHCO$_3$ (20 mL) and the aqueous phase was extracted with EtOAc (3×25 mL). The combined organic extracts were washed with brine, dried over anhydrous MgSO$_4$, and filtered. Concentration of the filtrate under reduced pressured followed by flash chromatography (hexane:EtOAc, 4:1) yielded cyclic allylic carbonate 81 (506.6 mg, 74%; 92% BORSM) as a colourless oil. $R_f$ 0.27 (hexane:EtOAc, 4:1); $[\alpha]_D^{20}$+67.1 (c 0.68, CHCl$_3$); IR (thin film) 2976, 2937, 2890, 1748, 1717, 1698, 1489, 1473, 1457, 1446, 1395, 1269, 1100, 1037, 1011, 945 cm$^{-1}$; $^1$H NMR (400 MHz, CDCl$_3$) δ 1.13-1.20 (12H, m), 3.52-3.70 (8H, m), 3.73 (3H, s), 3.85 (1H, dd, J=3.6, 7.9 Hz), 4.02-4.08 (2H, m), 4.12 (2H, s), 4.64 (2H, s), 4.72 (2H, s), 4.75 (1H, s), 4.81 (2H, dd, J=6.6, 9.5 Hz), 4.90 (1H, d, J=6.8 Hz), 5.32 (1H, s), 5.88 (1H, d, J=3.3 Hz); $^{13}$C NMR (100 MHz, CDCl$_3$) δ 15.0 (CH$_3$), 15.0 (CH$_3$), 15.1 (CH$_3$), 15.2 (CH$_3$), 54.8 (CH$_3$), 63.4 (CH$_2$), 63.5 (CH$_2$), 64.1 (CH$_2$), 64.2 (CH$_2$), 66.9 (CH$_2$), 71.6 (CH), 73.6 (CH), 76.7 (CH), 94.7 (CH$_2$), 94.7 (CH$_2$), 96.1 (CH$_2$), 96.5 (CH$_2$), 120.4 (CH), 140.8 (C), 155.5 (C); MS (ESI) m/z (relative intensity) 489 ([M+Na]$^+$, 100); HRMS (ESI) calcd for $C_{21}H_{38}O_{11}$ [M+Na]$^+$ 489.2306, found 489.2310.

Example 10

Cyclohexene 125

To a mixture of allylic chloride 60 (11.4 mg, 0.027 mmol) and boronic acid 124 (28.3 mg, 0.097 mmol) in degassed 1,4-dioxane (0.12 mL) was added Pd(dba)$_2$ (0.8 mg, 0.0015 mmol) and K$_2$CO$_3$ (13.5 mg, 0.097 mmol) sequentially. The reaction mixture was degassed for 3 times and stirred for 48 h at room temperature under nitrogen. Concentration of the mixture followed by flash chromatography (hexane:EtOAc, 7:1.5) yielded cyclohexene 125 (15.1 mg, 88%) as a colorless oil: $[\alpha]_D^{20}$+30.6 (c 0.67, CHCl$_3$); $R_f$ 0.30 (hexane:EtOAc, 7:2); IR (thin film) 2975, 2928, 2881, 1511, 1478, 1391, 1244, 1178, 1098, 1041, 821 cm$^{-1}$; $^1$H NMR (400 MHz, CDCl$_3$) δ 0.99 (3H, t, J=7.0 Hz), 1.22-1.28 (9H, m), 1.42 (3H, t, J=7.0 Hz), 2.96-3.04 (1H, m), 3.26-3.34 (1H, m), 3.60-3.75 (6H, m), 3.79 (1H, br s), 3.99-4.09 (5H, m), 4.13-4.19 (4H, m), 4.30 (1H, d, J=12.2 Hz), 4.54 (1H, d, J=7.1 Hz), 4.72 (2H, q, J=6.6 Hz), 4.79-4.88 (3H, m), 4.93 (1H, d, J=7.0 Hz), 5.93 (1H, s), 6.82 (2H, d, J=8.6 Hz), 7.09-7.13 (4H, m), 7.32 (1H, d, J=8.1 Hz); $^{13}$C NMR (100 MHz, CDCl$_3$) δ 15.0 (CH$_3$), 15.1 (CH$_3$), 15.2 (CH$_3$), 15.3 (CH$_3$), 29.8 (CH$_2$), 38.5 (CH$_2$), 41.8 (CH), 63.1 (CH$_2$), 63.5 (CH$_2$), 63.5 (CH$_2$), 63.9 (CH$_2$), 64.0 (CH$_2$), 68.3 (CH$_2$), 72.6 (CH), 74.1 (CH), 74.3 (CH), 94.3 (CH$_2$), 94.3 (CH$_2$), 94.9 (CH$_2$), 95.7 (CH$_2$), 114.5 (CH), 127.8 (CH), 128.9 (CH), 129.2 (CH), 129.8 (CH), 131.7 (C), 132.2 (CH), 132.6 (C), 134.1 (C), 138.7 (C), 139.8 (C), 157.5 (C); MS (ESI) m/z (relative intensity) 659 ([M+Na]$^+$, 100); HRMS (ESI) calcd for $C_{24}H_{49}ClO_9$ [M+Na]$^+$ 659.2957, found 659.2938.

Example 11

Tetraol 148

To a stirred solution of cyclohexene 125 (51.5 mg, 0.081 mmol) in EtOH (2 mL) was added 1M HCl (aq) (2 mL) at room temperature. The mixture was stirred at 50° C. for 12 h. Concentration of the reaction mixture under reduced pressure followed by flash chromatography (CHCl$_3$:MeOH, 15:1) furnished tetraol 148 (27.9 mg, 85%) as a colorless oil: $[\alpha]_D^{20}$+99.3 (c 0.48, CHCl$_3$); $R_f$ 0.47 (CHCl$_3$:MeOH, 9:1); IR (thin film) 3366, 2921, 1585, 1511, 1475, 1247, 1176, 1108, 1051, 1018, 834, 625 cm$^{-1}$; $^1$H NMR (700 MHz, CD$_3$OD) δ 1.35 (3H, t, J=7.0 Hz), 3.63 (1H, dd, J=9.2, 6.3 Hz), 3.72 (1H, t, J=5.0 Hz), 3.82 (1H, dd, J=9.4, 5.9 Hz), 3.97-4.03 (4H, m), 4.09 (1H, d, J=6.2 Hz), 4.20 (1H, d, J=13.7 Hz), 4.27 (1H, d, J=13.6 Hz), 5.72 (1H, d, J=4.4 Hz), 6.79 (2H, d, J=8.5 Hz), 7.08-7.09 (3H, m), 7.16 (1H, d, J=1.7 Hz), 7.28 (1H, d, J=8.2 Hz); $^{13}$C NMR (100 MHz, CD$_3$OD) δ 15.2 (CH$_3$), 39.3 (CH$_2$), 47.2 (CH), 63.6 (CH$_2$), 64.4 (CH$_2$), 72.1 (CH), 73.4 (CH), 74.1 (CH), 115.4 (CH), 124.4 (CH), 129.7 (CH), 130.7 (CH), 130.8 (CH), 133.0 (C), 133.4 (C), 134.5 (CH), 139.5 (C), 139.6 (C), 141.3 (C), 158.8 (C); MS (ESI) m/z (relative intensity) 427 ([M+Na]$^+$, 100); HRMS (ESI) calcd for $C_{22}H_{25}ClO_5$ [M+Na]$^+$ 427.1283, found 427.1289.

Example 12

Tetraol 123

To a solution of cyclohexene 125 (187 mg, 0.293 mmol) in THF/H$_2$O (1:1, 30 mL) was added NaOAc (2.40 g, 29.3 mmol) and p-TsNHNH$_2$ (2.72 g, 14.6 mmol) at room temperature. The mixture was heated to 80° C. for 48 h. The reaction was quenched by addition of saturated NaHCO$_3$ solution (50 mL) at room temperature. The aqueous phase was extracted with EtOAc (3×50 mL) and the combined organic extracts were washed with brine, dried over anhydrous MgSO$_4$, and filtered. Concentration of the filtrate followed by flash chromatography (hexane:EtOAc, 7:2) yielded an inseparable mixture of cyclohexane 149 and 150 (152 mg, 82%) as a colorless oil: $R_f$ 0.33 (hexane:EtOAc, 7:2). To a stirred solution of the mixture of cyclohexane 149 and 150 (89.9 mg, 0.141 mmol) in EtOH (3 mL) was added 1M HCl (aq) (3 mL) at room temperature. The mixture was stirred at 50° C. for 3 h. Concentration of the reaction mixture under reduced pressure followed by flash chromatography (CHCl$_3$:MeOH, 9:1) furnished tetraol 123 (5.4 mg, 9%) as a pale yellow oil: $[\alpha]_D^{20}$−32.8 (c 0.32, CHCl$_3$); $R_f$ 0.25 (CHCl$_3$:MeOH, 9:1); IR (thin film) 3415, 2922, 1631, 1510, 1478, 1243, 1176, 1121, 1048, 976, 816 cm$^{-1}$; $^1$H NMR (700 MHz, CD$_3$OD) δ 1.35 (3H, t, J=7.0 Hz), 1.47 (1H, dt, J=12.8, 3.3 Hz), 1.98 (1H, q, J=13.0 Hz), 2.08-2.13 (1H, m), 3.08 (1H, dt, J=13.1, 2.9 Hz), 3.57 (1H, dd, J=10.6, 6.5 Hz), 3.71 (1H, dd, J=10.6, 7.0 Hz), 3.79 (1H, br s), 3.93 (1H, br s), 3.96-4.00 (5H, m), 6.79 (2H, dt, J=8.7, 2.9 Hz), 7.08 (2H, d, J=8.6 Hz), 7.17 (1H, dd, J=8.2, 2.1 Hz), 7.19 (1H, d, J=2.0 Hz), 7.28 (1H, d, J=8.2 Hz); $^{13}$C NMR (100 MHz, CD$_3$OD) δ 15.2 (CH$_3$), 23.6 (CH$_2$), 39.3 (CH$_2$), 40.4 (CH), 42.8 (CH), 64.4 (CH$_2$), 65.1 (CH$_2$), 71.9 (CH), 72.0 (CH), 76.1 (CH), 115.4 (CH), 128.8 (CH), 130.0 (CH), 130.8 (CH), 132.3 (CH), 132.7 (C), 133.1 (C), 139.8 (C), 144.3 (C), 158.8 (C); MS (ESI) m/z (relative intensity) 428 ([M+Na]$^+$, 100); HRMS (ESI) calcd for $C_{22}H_{27}ClO_5$ [M+Na]$^+$ 429.1439, found 429.1440.

Example 13

Tetraol 151

To a solution of cyclohexene 125 (187 mg, 0.293 mmol) in THF/H$_2$O (1:1, 30 mL) was added NaOAc (2.40 g, 29.3 mmol) and p-TsNHNH$_2$ (2.72 g, 14.6 mmol) at room temperature. The mixture was heated to 80° C. for 48 h. The reaction was quenched by addition of saturated NaHCO$_3$ solution (50 mL) at room temperature. The aqueous phase was extracted with EtOAc (3×50 mL) and the combined organic extracts were washed with brine, dried over anhydrous MgSO$_4$, and filtered. Concentration of the filtrate followed by flash chromatography (hexane:EtOAc, 7:2) yielded an inseparable mixture of cyclohexane 149 and 150 (152 mg, 82%) as a colorless oil: R$_f$ 0.33 (hexane:EtOAc, 7:2). To a stirred solution of the mixture of cyclohexane 149 and 150 (89.9 mg, 0.141 mmol) in EtOH (3 mL) was added 1M HCl (aq) (3 mL) at room temperature. The mixture was stirred at 50° C. for 3 h. Concentration of the reaction mixture under reduced pressure followed by flash chromatography (CHCl$_3$:MeOH, 9:1) furnished tetraol 151 (35.2 mg, 62%) as a colorless oil: $[\alpha]_D^{20}$+29.4 (c 0.99, CHCl$_3$); R$_f$ 0.23 (CHCl$_3$:MeOH, 9:1); IR (thin film) 3402, 2919, 1539, 1512, 1478, 1247, 1174, 1077, 1036, 829 cm$^{-1}$; $^1$H NMR (400 MHz, CD$_3$OD) δ 1.35 (3H, t, J=7.0 Hz), 1.64 (1H, ddd, J=14.4, 10.2, 4.8 Hz), 1.78-1.86 (1H, m), 2.12 (1H, dt, J=14.0, 4.6 Hz), 3.37-3.41 (1H, m), 3.60 (1H, dd, J=10.8, 6.7 Hz), 3.69 (1H, dd, J=11.0, 4.4 Hz), 3.73-3.75 (2H, m), 3.96-4.01 (4H, m), 6.80 (2H, d, J=8.6 Hz), 7.08 (2H, d, J=8.5 Hz), 7.26-7.33 (3H, m); $^{13}$C NMR (100 MHz, CD$_3$OD) δ 15.2 (CH$_3$), 29.3 (CH$_2$), 39.3 (CH$_2$), 42.3 (CH), 43.1 (CH), 64.4 (CH$_2$), 64.5 (CH$_2$), 75.2 (CH), 75.7 (CH), 75.8 (CH), 115.4 (CH), 129.8 (CH), 129.8 (CH), 130.8 (CH), 132.6 (C), 133.0 (C), 133.6 (CH), 139.7 (C), 142.4 (C), 158.7 (C); MS (ESI) m/z (relative intensity) 429 ([M+Na]$^+$, 100); HRMS (ESI) calcd for C$_{21}$H$_{26}$O$_5$ [M+Na]$^+$ 429.1439, found 429.1435.

Example 14

Cyclohexene 116

To a mixture of cyclic allylic carbonate 81 (71.7 mg, 0.154 mmol) and aryl boronic acid 88 (141.1 mg, 0.486 mmol) in degassed 1,4-dioxane (0.19 mL) was added Pd(dba)$_2$ (5.5 mg, 0.0096 mmol) and K$_2$CO$_3$ (68.1 mg, 0.493 mmol) sequentially. The reaction mixture was degassed for 3 times and stirred for 72 h at rt under nitrogen. Concentration of the reaction mixture under reduced pressured followed by flash chromatography (hexane:EtOAc, 7:2) yielded cyclohexene 116 (82.8 mg, 85%) as a colourless oil. R$_f$ 0.37 (hexane:EtOAc, 7:2); $[\alpha]_D^{20}$-33.7 (c 0.55, CHCl$_3$); IR (thin film) 2980, 2919, 2852, 1733, 1716, 1698, 1684, 1653, 1647, 1558, 1541, 1521, 1508, 1473, 1457, 1244, 1142, 1115, 1018, 835 cm$^{-1}$; $^1$H NMR (400 MHz, CDCl$_3$) δ 0.79 (3H, t, J=7.0 Hz), 1.18-1.25 (9H, m), 1.39 (3H, t, J=6.9 Hz), 2.80-2.85 (1H, m), 2.97-3.05 (1H, m), 3.42 (1H, d, J=7.8 Hz), 3.41-3.80 (8H, m), 3.87 (1H, t, J=8.3 Hz), 3.96-4.01 (4H, m), 4.09 (1H, d, J=13.1 Hz), 4.19 (1H, d, J=13.1 Hz), 4.30 (1H, d, J=6.1 Hz), 4.35 (1H, d, J=6.8 Hz), 4.66 (2H, s), 4.81-4.86 (3H, m), 4.96 (1H, d, J=6.6 Hz), 5.58 (1H, s), 6.79 (2H, d, J=8.4 Hz), 6.70-7.04 (2H, m), 7.08 (2H, d, J=8.3 Hz), 7.29 (1H, d, J=8.1 Hz); $^{13}$C NMR (100 MHz, CDCl$_3$) δ 14.8 (CH$_3$), 15.0 (CH$_3$), 15.2 (CH$_3$), 15.3 (CH$_3$), 15.3 (CH$_3$), 38.5 (CH$_2$), 48.9 (CH), 63.6 (CH$_2$), 63.6 (CH$_2$), 64.4 (CH$_2$), 64.5 (CH$_2$), 67.0 (CH$_2$), 78.5 (CH), 80.2 (CH), 82.8 (CH), 94.3 (CH$_2$), 95.8 (CH$_2$), 96.8 (CH$_2$), 96.9 (CH$_2$), 114.5 (CH), 127.4 (CH), 127.7 (CH), 129.7 (CH), 129.9 (CH), 131.5 (C), 131.7 (CH), 132.6 (C), 135.3 (C), 139.0 (C), 141.3 (C), 157.5 (C); MS (ESI) m/z (relative intensity) 659 ([M+Na]$^+$, 100); HRMS (ESI) calcd for C$_{21}$H$_{38}$O$_{11}$ [M+Na]$^+$ 659.2957, found 659.2963.

Example 15

Tetraol 118

To a solution of cyclohexene 116 (66.6 mg, 0.105 mmol) in EtOH (1.5 mL) was added 1M HCl (aq) (1.5 mL) at t. The reaction mixture was stirred at 50° C. for 3 h. Concentration of the reaction mixture under reduced pressure followed by flash chromatography (CHCl$_3$:MeOH, 9:1) yield tetraol 118 (36.9 mg, 87%) as a white solid. R$_f$ 0.22 (CHCl$_3$:MeOH, 9:1); $[\alpha]_D^{20}$-97.1 (c 0.56, CHCl$_3$); IR (thin film) 3366, 2979, 2919, 1717, 1699, 1685, 1654, 1647, 1637, 1617, 1559, 1541, 1509, 1489, 1474, 1458, 1437, 1419, 1396, 1387, 1244, 1115, 1046, 991, 837 cm$^{-1}$; $^1$H NMR (400 MHz, CD$_3$OD) δ 1.35 (3H, t, J=7.0 Hz), 3.45 (1H, t, J=9.6 Hz), 3.57 (1H, dd, J=7.8, 9.9 Hz), 3.95-4.06 (5H, m), 4.11 (1H, d, J=13.8 Hz), 4.24 (2H, d, J=12.3 Hz), 5.50 (1H, s), 6.79 (2H, dd, J=2.0, 6.7 Hz), 7.08 (3H, d, 8.8 Hz), 7.15 (1H, d, J=2.1 Hz), 7.31 (1H, d, J=8.2 Hz); $^{13}$C NMR (100 MHz, CD$_3$OD) δ 15.2 (CH$_3$), 39.2 (CH$_2$), 50.7 (CH), 63.1 (CH$_2$), 64.4 (CH$_2$), 74.0 (CH), 76.9 (CH), 79.3 (CH), 115.4 (CH), 125.8 (CH), 128.9 (CH), 130.4 (CH), 130.8 (CH), 132.6 (CH), 133.0 (C), 133.3 (C), 140.2 (C), 140.8 (C), 143.4 (C), 158.9 (C); MS (ESI) m/z (relative intensity) 427 ([M+Na]$^+$, 100); HRMS (ESI) calcd for C$_{21}$H$_{38}$O$_{11}$ [M+Na]$^+$ 427.1283, found 427.1284.

Example 16

Tetraol 80

To a stirred solution of cyclohexene 116 (27.2 mg, 0.043 mmol) and NaOAc (353 mg, 4.30 mmol) in THF/H$_2$O (1:1, 5 mL) was added pTsNHNH$_2$ (400 mg, 2.15 mmol) at 70° C. over 4 h. The reaction mixture was heated at 70° C. for 30 min after the addition of pTsNHNH$_2$ was completed. The reaction was quenched with saturated NaHCO$_3$ (20 mL) and the aqueous phase was extracted with Et$_2$O (3×25 mL). The combined organic extracts were washed with brine, dried over anhydrous MgSO$_4$, and filtered. Concentration of the filtrate under reduced pressured followed by flash chromatography (hexane:EtOAc, 7:2) yielded an inseparable mixture of cyclohexanes 121 and 122 (22.7 mg, 83%) as a colourless oil. R$_f$ 0.33 (hexane:EtOAc, 7:2). To a solution of mixture of cyclohexanes 121 and 122 (19.8 mg, 0.031 mmol) in EtOH (1.5 mL) was added 1M HCl (aq) (1.5 mL) at rt. The reaction mixture was stirred at 50° C. for 3 h. Concentration of the reaction mixture under reduced pressure followed by preparative TLC (CHCl$_3$:MeOH, 9:1) yield tetraol 80 (8.2 mg, 65%) as a white solid. R$_f$ 0.25 (CHCl$_3$:MeOH, 9:1); $[\alpha]_D^{20}$-18.6 (c 0.44, CHCl$_3$); IR (thin film) 3421, 2926, 2849, 1653, 1647, 1636, 1559, 1541, 1508, 1474, 1457, 1244, 1111, 1044, 843 cm$^{-1}$; $^1$H NMR (700 MHz, CD$_3$OD) δ 1.36 (3H, t, J=7.0 Hz), 1.39 (1H, q, J=13.0 Hz), 1.62-1.67 (1H, m), 1.80 (1H, dt, J=13.7, 3.4 Hz), 2.56 (1H, ddd, J=3.4, 10.6, 12.7 Hz), 3.27-3.29 (1H, m), 3.32-3.33 (1H, m), 3.44 (1H, dd, J=9.0, 10.2 Hz), 3.56-3.60 (1H, m), 3.75 (1H, dd, J=3.7, 10.8 Hz), 3.98 (2H, q, J=7.0 Hz), 4.00 (2H, s), 6.80 (2H, d, J=8.5 Hz), 7.08-7.13 (4H, m), 7.30 (1H, d, J=8.2 Hz); $^{13}$C NMR (100 MHz, CD$_3$OD) δ 15.2 (CH$_3$), 34.2 (CH$_2$), 39.2 (CH$_2$), 45.4 (CH), 49.4 (CH), 64.3 (CH$_2$), 64.4 (CH$_2$), 75.0 (CH), 77.3 (CH), 81.1 (CH), 115.4 (CH), 128.2 (CH), 130.3 (CH), 130.8 (CH), 132.0 (CH), 132.9 (C), 133.0 (C), 140.1 (C), 143.6 (C), 158.8 (C); MS (ESI) m/z (relative intensity) 429 ([M+Na]$^+$, 100); HRMS (ESI) calcd for C$_{21}$H$_{38}$O$_{11}$ [M+Na]$^+$ 429.1439, found 429.1438.

Example 17

Tetraol 130

To a stirred solution of cyclohexene 116 (27.2 mg, 0.043 mmol) and NaOAc (353 mg, 4.30 mmol) in THF/H$_2$O (1:1, 5 mL) was added pTsNHNH$_2$ (400 mg, 2.15 mmol) at 70° C. over 4 h. The reaction mixture was heated at 70° C. for 30 min after the addition of pTsNHNH$_2$ was completed. The reaction was quenched with saturated NaHCO$_3$ (20 mL) and the aqueous phase was extracted with E₂tO (3×25 mL). The combined organic extracts were washed with brine, dried over anhydrous MgSO₄, and filtered. Concentration of the filtrate under reduced pressured followed by flash chromatography (hexane:EtOAc, 7:2) yielded an inseparable mixture of cyclohexanes 121 and 122 (22.7 mg, 83%) as a colourless oil. $R_f$ 0.33 (hexane:EtOAc, 7:2). To a solution of mixture of cyclohexanes 121 and 122 (19.8 mg, 0.031 mmol) in EtOH (1.5 mL) was added 1M HCl (aq) (1.5 mL) at rt. The reaction mixture was stirred at 50° C. for 3 h. Concentration of the reaction mixture under reduced pressure followed by preparative TLC (CHCl₃:MeOH, 9:1) yield tetraol 130 (3.1 mg, 25%) as a white solid. $R_f$ 0.24 (CHCl₃:MeOH, 9:1); $[\alpha]_D^{20}$ –13.5 (c 0.25, CHCl₃); IR (thin film) 3421, 2961, 2922, 2851, 1653, 1647, 1636, 1559, 1541, 1508, 1473, 1458, 1243, 1111, 1044 cm⁻¹; ¹H NMR (400 MHz, CD₃OD) δ 1.36 (3H, t, J=7.0 Hz), 1.59 (1H, td, J=13.7, 4.1 Hz), 1.95 (1H, dt, J=14.4, 3.2 Hz), 2.19-2.24 (1H, m), 2.71-2.78 (1H, m), 3.27-3.29 (1H, m), 3.40-3.43 (2H, m), 3.64-3.77 (3H, m), 3.96-4.00 (4H, m), 6.80 (2H, d, J=8.6 Hz), 7.08-7.15 (4H, m), 7.30 (1H, d, J=8.2 Hz); ¹³C NMR (100 MHz, CD₃OD) α 15.2 (CH₃), 32.1 (CH₂), 39.2 (CH₂), 43.3 (CH), 45.2 (CH), 60.3 (CH₂), 64.4 (CH₂), 75.2 (CH), 77.0 (CH), 78.2 (CH), 115.4 (CH), 128.2 (CH), 130.3 (CH), 130.8 (CH), 132.2 (CH), 132.9 (C), 133.0 (C), 140.1 (C), 143.6 (C), 158.8 (C); MS (ESI) m/z (relative intensity) 429 ([M+Na]⁺, 100); HRMS (ESI) calcd for C₂₁H₃₈O₁₁ [M+Na]⁺ 429.1439, found 429.1441.

Example 18

Biological Data (Potency) for the SGLT2 Inhibitors

¹⁴C-α-methyl-D-glucopyranoside (¹⁴C-AMG) was purchased from PerkinElmer Inc. (Utah, USA). Dulbeccos Modified Eagle's Medium (DMEM), fetal bovine serum (FBS), penicillin-streptomycin (PS) and trypsin-EDTA were purchased from Invitrogen of Thermo Fisher Scientific Inc. (Massachusetts, USA). Phloridzin dihydrate, choline chloride, G418 disulfate salt (G418) and bicinchoninic acid solution (BCA) were purchased from Sigma-Aldrich Co. (Missouri, USA).

SGLT1 (S1)- or SGLT2 (S2)-expressing cells were developed in our laboratory by transfecting, respectively, SLC5A1 (NM_000343) or SLC5A2 (NM_003041) human cDNA clone (Origene Technologies Inc., Maryland, USA) into COS-7 cells (monkey fibroblast-like kidney cells, CRL-1651, ATCC, Manassas, USA). The cells were cultured in DMEM supplemented with 10% FBS, 1% PS and G418 (1 mg/ml), and kept in 37° C. humidified incubator supplied with 5% CO₂. For the uptake assay, the cells (2×10⁵ cells/well) were seeded in 24-well plate and incubated overnight. Then, each well was added with the testing samples at different concentrations and 100 μCi/ml ¹⁴C-AMG. The cells were incubated in sodium buffer (140 mM NaCl, 2 mM KCl, 1 mM MgCl₂, 1 mM CaCl₂, and 10 mM Hepes/Tris, pH 7.5) at 37° C. for 2 hours. After incubation, the plates were washed three times with cold choline stop buffer (140 mM choline chloride, 2 mM KCl, 1 mM MgCl₂, 1 mM CaCl₂, and 10 mM Hepes/Tris, pH 7.5) containing 100 μM phlorizin dihydrate. After removing all buffer, the cells were then solubilized with 150 μL NaOH (0.5 M) and followed by 150 μL HCl (0.5 M). Then, 200 μL solution was taken out for the measurement of radioactivity and 30 μL solution was used to measure the protein content by BCA protein assay, which was used to normalize the cell number in each well. The amount of glucose uptake was expressed as cpm/mg protein.

In Li's thesis:

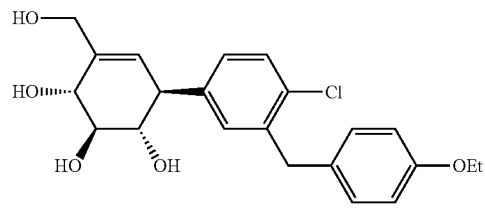

118

IC₅₀ (SGLT1): 9930 nM
IC₅₀ (SGLT2): 24.0 nM

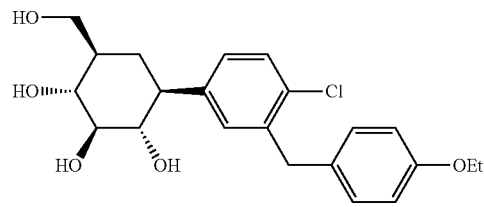

80

IC₅₀ (SGLT1): 8740 nM
IC₅₀ (SGLT2): 438 nM

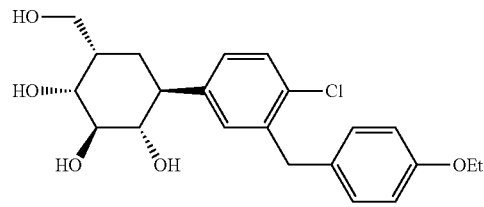

130

IC₅₀ (SGLT1): 9990 nM
IC₅₀ (SGLT2): 667 nM

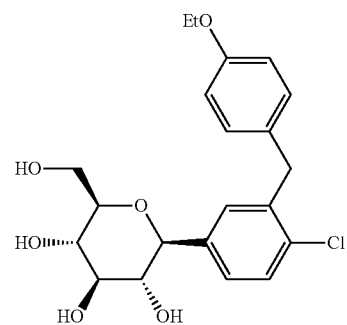

Reference compound
IC₅₀ (SGLT1): 526 nM
IC₅₀ (SGLT2): 0.6 nM

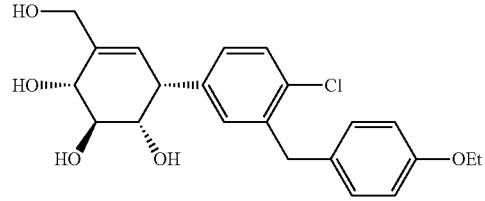

148

IC₅₀ (SGLT1): >50000 nM
IC₅₀ (SGLT2): >10000 nM

-continued

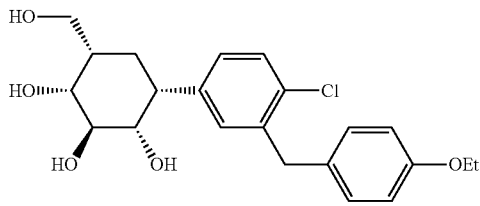

123

IC$_{50}$ (SGLT1): >50000 nM
IC$_{50}$ (SGLT2): >10000 nM

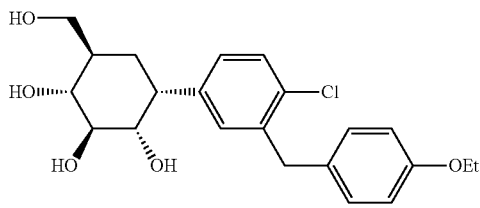

151

IC$_{50}$ (SGLT1): >50000 nM
IC$_{50}$ (SGLT2): >10000 nM

All patents, patent applications, and other publications, including GenBank Accession Numbers, cited in this application are incorporated by reference in the entirety for all purposes.

LIST OF REFERENCES

1. Kanai, Y.; Lee, W. S.; You, G.; Brown, D.; Hediger, M. A. *J. Clin. Invest.* 1994, 93, 397-404.
2. Lee, W. S.; Kanai, Y.; Wells, R. G.; Hediger, M. A. *J. Biol. Chem.* 1994, 269, 12032-12039.
3. Chao, E. C.; Henry, R. R. *Nat. Rev. Drug Discov.* 2010, 9, 551-559.
4. Jones, D. *Nat. Rev. Drug Discov.* 2011, 10, 645-646.
5. Nair, S.; Wilding, J. P. H. *J. Clin. Endocrinol. Metab.* 2010, 95, 34-42.
6. Hall, D. G. *Boronic Acids—Preparation, Applications in Organic Synthesis and Medicine*; Hall, D. G., Ed.; Wiley-VCH: Weinheim, Germany, 2005, pp 1-99.
7. Bäckvall, J.-E.; Granberg, K. L.; Heumann, A. *Isr. J. Chem.* 1991, 31, 17-24.
8. Kwong, S. K. PhD. Thesis, The Chinese University of Hong Kong, 2006.
9. Chen, Y. MPhil. Thesis, The Chinese University of Hong Kong, 2010.
10. Shing, T.; Chen, Y.; Ng, W. *Synlett* 2011, 2011, 1318-1320.
11. Gerbino, D. C.; Mandolesi, S. D.; Schmalz, H.-G.; Podestá, J. C. *European Journal of Organic Chemistry* 2009, 2009, 3964-3972.
12. Bouyssi, D.; Gerusz, V.; Balme, G. *European Journal of Organic Chemistry* 2002, 2002, 2445-2448.
13. Li, C.; Xing, J.; Zhao, J.; Huynh, P.; Zhang, W.; Jiang, P.; Zhang, Y. *J. Organic Letters* 2012, 14, 390-393.
14. Nishikata, T.; Lipshutz, B. H. *Journal of the American Chemical Society* 2009, 131, 12103-12105.
15. Kayaki, Y.; Koda, T.; Ikariya, T. *European Journal of Organic Chemistry* 2004, 2004, 4989-4993.
16. Li, M.-B.; Wang, Y.; Tian, S.-K. *Angewandte Chemie* 2012, 124, 3022-3025.
17. Ohmiya, H.; Makida, Y.; Li, D.; Tanabe, M.; Sawamura, M. *Journal of the American Chemical Society* 2010, 132, 879-889.
18. Pigge, C. F.; Search. *Synthesis* 2010, 2010, 1745-1762.
19. Ng, W.-L. PhD. Thesis, The Chinese University of Hong Kong, 2014.
20. Ohtake, Y.; Sato, T.; Matsuoka, H.; Kobayashi, T.; Nishimoto, M.; Taka, N.; Takano, K.; Yamamoto, K.; Ohmori, M.; Higuchi, T.; Murakata, M.; Morikawa, K.; Shinma, N.; Suzuki, M.; Hagita, H.; Ozawa, K.; Yamaguchi, K.; Kato, M.; Ikeda, S. *Bioorg. Med. Chem.* 2012, 20, 4117-4127.
21. Wright, S. W.; Hageman, D. L.; McClure, L. D. *The Journal of Organic Chemistry* 1994, 59, 6095-6097.
22. Hudlický, M. *Reductions in organic chemistry*; Ellis Horwood Ltd.: New York, 1984, pp 1-13.
23. Ukisu, Y.; Miyadera, T. *Journal of Molecular Catalysis A: Chemical* 1997, 125, 135-142.
24. Aramendia, M. A.; Borau, V.; García, I. M.; Jiménez, C.; Marinas, A.; Marinas, J. M.; Urbano, F. J. *Comptes Rendus de l'Academie des Sciences—Series IIC—Chemistry* 2000, 3, 465-470.
25. Desmarets, C.; Kuhl, S.; Schneider, R.; Fort, Y. *Organometallics* 2002, 21, 1554-1559.
26. Léger, B.; Nowicki, A.; Roucoux, A.; Rolland, J.-P. *Journal of Molecular Catalysis A: Chemical* 2007, 266, 221-225.
27. Washburn, W. N. *Journal of Medicinal Chemistry* 2009, 52, 1785-1794.
28. Webster, R.; Boyer, A.; Fleming, M. J.; Lautens, M. *Organic Letters* 2010, 12, 5418-5421.
29. Hog, D. T.; Mayer, P.; Trauner, D. *The Journal of Organic Chemistry* 2012, 77, 5838-5843.
30. Willis, C.; Back, R. A. *Canadian Journal of Chemistry* 1973, 51, 3605-3619.

TABLE 1

Conditions for chlorination of β-allylic alcohol 52.

| Entry | Conditions | Results |
|-------|------------|---------|
| 1 | NCS, PPh$_3$, THF, reflux, 8 h | No reaction |
| 2 | PPh$_3$, CCl$_4$, Imidazole, CH$_3$CN, reflux, 18 h | No reaction |
| 3 | MsCl, Et$_3$N, CH$_2$Cl$_2$, 0° C., 15 min | Decomposed upon workup |
| 4 | MsCl, Et$_3$N, 3Å MS, LiCl, CH$_2$Cl$_2$, 0° C. to rt, 6 h | Decomposed |
| 5 | MsCl, Et$_3$N, 3Å MS, LiCl, THF, 0° C. to rt, 6 h | No reaction |
| 6 | 1. MsCl, Et$_3$N, CH$_2$Cl$_2$, 0° C.<br>2. $^n$Bu$_4$NCl, 3Å MS, 0° C. to rt, 30 min | 58% |
| 7 | MsCl, pyridine, 3Å MS, nBu$_4$NCl, 0° C. to rt, 12 h | 71% |
| 8 | MsCl, Et$_3$N, 3Å MS, nBu$_4$NCl, CH$_2$Cl$_2$, 0° C. to rt, 30 min | 81% |

TABLE 2

Chlorination of cyclic β-allylic alcohol 87

87 → 109 (Conditions)

| Entry | Conditions | Results |
|---|---|---|
| 1 | SOCl₂, Et₂O, 0° C. to rt, 30 min | Decomposed |
| 2 | SOCl₂, pyridine, Et₂O, 0° C. to rt, 30 min | Decomposed |
| 3 | SOCl₂, 0° C. to rt, 30 min | Complex mixture |
| 4 | 1. MsCl, Et₃N, CH₂Cl₂, 3Å MS, 0° C. 30 min<br>2. nBu₄NCl (in CH₂Cl₂), 0° C. to rt, 2 h | Decomposed |
| 5 | MsCl, Et₃N, nBu₄NCl, CH₂Cl₂, 3Å MS, 0° C. to rt, 3 h | Decomposed |
| 6 | MsCl, pyridine, nBu₄NCl, 3Å MS, 0° C. to rt, 3 h | Decomposed |

TABLE 3

Preparation of cyclic allylic carbonate 81

86 → 81 (Conditions)

| Entry | Conditions | Results |
|---|---|---|
| 1 | Methyl chloroformate, Et₃N, CH₂Cl₂, 0° C. to rt, 24 h | 12% |
| 2 | Methyl chloroformate, Et₃N, CH₂Cl₂, 3Å MS, 0° C. to rt, 24 h | 14% |
| 3 | Methyl chloroformate, pyridine, CH₂Cl₂, 0° C. to rt, 24 h | 65% (BORSM 80%) |
| 4 | Methyl chloroformate, pyridine, 0° C. to rt, 24 h | 74% (BORSM 92%) |
| 5 | 1. nBuLi, THF, −78° C. to 0° C., 30 min<br>2. Methyl chloroformate, 0° C. to rt, 24 h | 51% |

TABLE 4

Suzuki-type coupling between allylic chloride 60 and aryl boronic acid derivatives

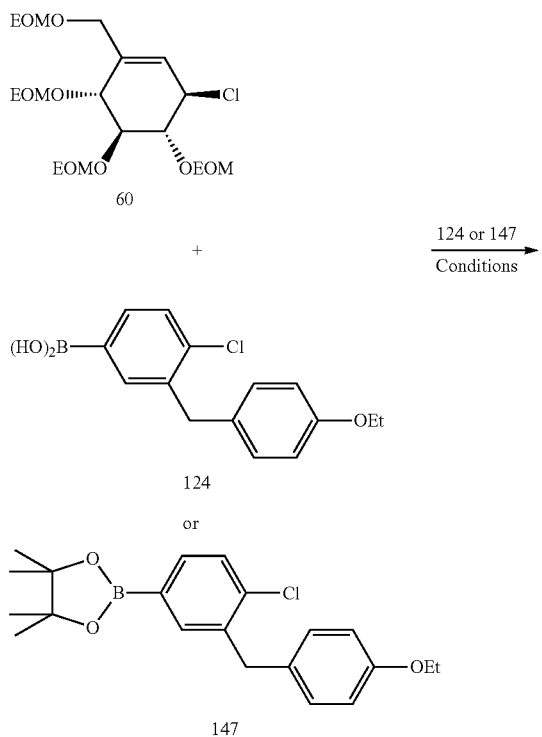

TABLE 4-continued

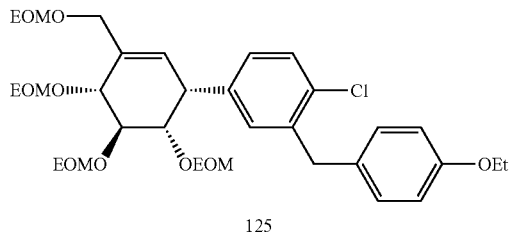

125

| Entry | Conditions | Results |
|---|---|---|
| 1 | 124, Pd(dba)$_2$, K$_2$CO$_3$, CHCl$_3$, rt, 2 d | 38% |
| 2 | 124, Pd(dba)$_2$, K$_3$PO$_4$·3H$_2$O, CHCl$_3$, rt, 1 d | 69% |
| 3 | 124, Pd(dba)$_2$, KF, CHCl$_3$, rt, 2 d | 62% |
| 4 | 124, Pd(dba)$_2$, K$_3$PO$_4$·3H$_2$O, 1,4-dioxane, rt, 2 d | 74% |
| 5 | 124, Pd(dba)$_2$, K$_2$CO$_3$, 1,4-dioxane, rt, 2 d | 88% |
| 6 | 147, Pd(dba)$_2$, K$_3$PO$_4$·3H$_2$O, 1,4-dioxane, rt, 2 d | 71% |
| 7 | 147, Pd(dba)$_2$, K$_2$CO$_3$, 1,4-dioxane, rt, 2 d | 22% |
| 8 | 147, Pd(dba)$_2$, K$_2$CO$_3$, CH$_3$CN, rt, 2 d | 24% |

TABLE 5

Hydrogenation of compound 125.

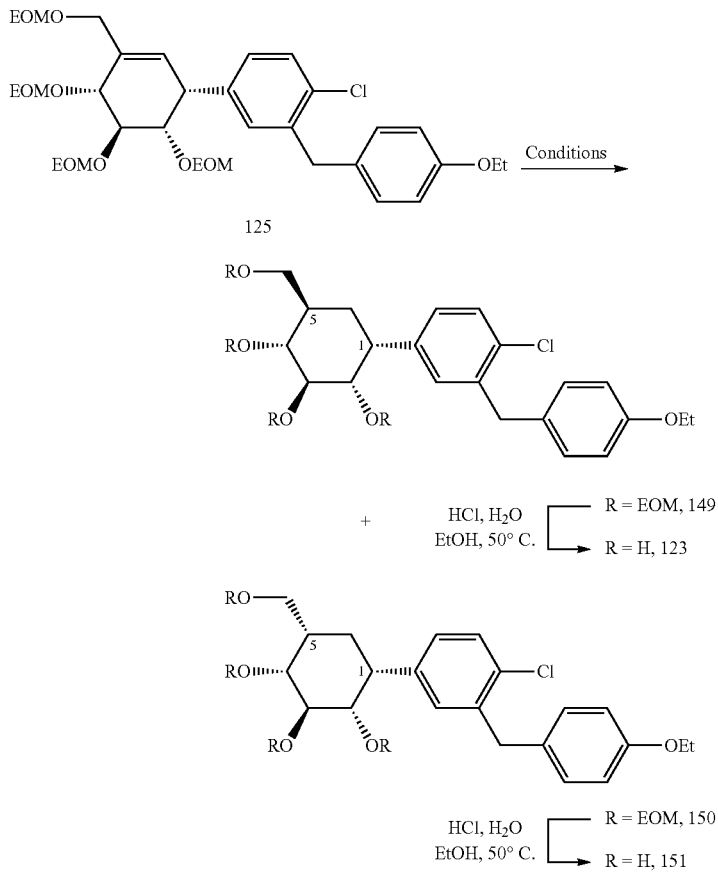

Results

| Entry | Conditions | Hydrogenation (149 + 150) | Over two steps |
|---|---|---|---|
| 1 | Ru/C (cat.), H$_2$, EtOH, rt | No reaction | — |
| 2 | Rh/C (cat.), H$_2$, EtOH, rt | No reaction | — |

TABLE 5-continued

| | | | |
|---|---|---|---|
| 3 | p-TsNHNH$_2$, NaOAc, THF/H$_2$O = 1/1, reflux | 82% | 123, 7%; 151, 51% |

TABLE 6

Screening of palladium sources and ligands for the Suzuki-type aryl-ally cross coupling reaction between cyclic allylic carbonate 81 and aryl boronic acid 88

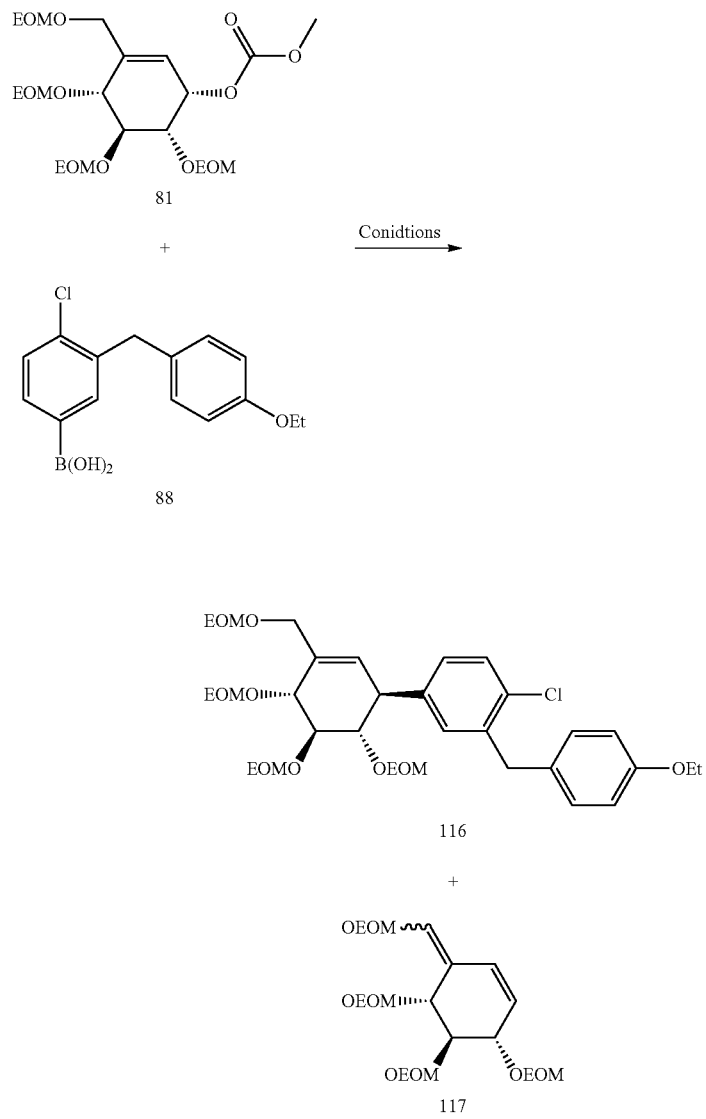

| Entry | Conditions | Results |
|---|---|---|
| 1 | Pd(OAc)$_2$, dppf, K$_2$CO$_3$, 1,4-dioxane, rt, 3.5 d | 116, 51%; 117, 29% |
| 2 | Pd/C, K$_2$CO$_3$, 1,4-dioxane, rt, 3 d | 116, 34%; 117, 33% |
| 3 | Pd(dba)$_2$, K$_2$CO$_3$, 1,4-dioxane, rt, 3 d | 116, 85%; 117, 7% |
| 4 | Pd(dba)$_2$, dppf, K$_2$CO$_3$, 1,4-dioxane, rt, 3 d | 116, 22%; 117, 47% |
| 5 | Pd(dba)$_2$, dppp, K$_2$CO$_3$, 1,4-dioxane, rt, 3.5 d | 116, 11%; 117, 57% |
| 6 | Pd(dba)$_2$, dppe, K$_2$CO$_3$, 1,4-dioxane, rt, 3 d | 116, 13%; 117, 58% |

TABLE 7

Screening of additives, solvents and temperature for the Suzuki-type aryl-ally cross coupling reaction between cyclic allylic carbonate 81 and aryl boronic acid 88

| Entry | Conditions | Results |
|---|---|---|
| 1 | Pd(dba)$_2$, K$_2$CO$_3$, 1,4-dioxane, rt, 3 d | 116, 85%; 117, 7% |
| 2 | Pd(dba)$_2$, KF, 1,4-dioxane, rt, 3 d | 116, 66%; 117, 13% |
| 3 | Pd(dba)$_2$, K$_3$PO$_4$•3H$_2$O, 1,4-dioxane, rt, 3.5 d | 116, 72%; 117, 15% |
| 4 | Pd(dba)$_2$, Na$_2$CO$_3$, 1,4-dioxane, rt, 3.5 d | 116, 70%; 117, 19% |
| 5 | Pd(dba)$_2$, Cs$_2$CO$_3$, 1,4-dioxane, rt, 3 d | 116, 67%; 117, 22% |
| 6 | Pd(dba)$_2$, K$_2$CO$_3$, THF, rt, 3 d | 116, 71%; 117, 20% |
| 7 | Pd(dba)$_2$, K$_2$CO$_3$, CH$_2$Cl$_2$, rt, 3.5 d | 116, 34%; 117, 41% |
| 8 | Pd(dba)$_2$, K$_2$CO$_3$, CHCl$_3$, rt, 3.5 d | 116, 38%; 117, 37% |
| 9 | Pd(dba)$_2$, K$_2$CO$_3$, Toluene, rt, 3 d | 116, 49%; 117, 32% |
| 10 | Pd(dba)$_2$, K$_2$CO$_3$, CH$_3$CN, rt, 4.5 d | 116, 22%; 117, 57% |
| 11 | Pd(dba)$_2$, K$_2$CO$_3$, 1,4-dioxane, 50° C., 1.5 d | 116, 35%; 117, 50% |

TABLE 8

Hydrogenation conditions mimicked on diarylmethane 40

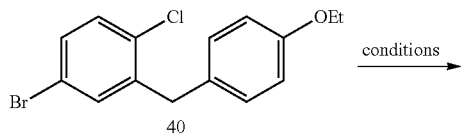 [SMILES: CCOc1ccc(Cc2cc(Br)ccc2Cl)cc1]

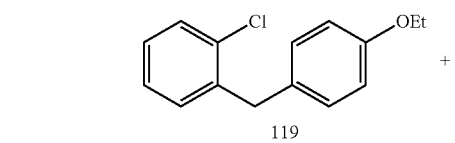 [SMILES: CCOc1ccc(Cc2ccccc2Cl)cc1]

| Entry | Conditions | Results |
|---|---|---|
| 1 | H$_2$, Pt$_2$O/C, EtOH, 3 h, rt | 120, 95% |
| 2 | H$_2$, Pd/C, EtOH, 3 h, rt | 120, 96% |
| 3 | H$_2$, Raney Ni, EtOH, 3 h, rt | 120, 92% |

TABLE 9

Hydrogenation of cyclohexene 116

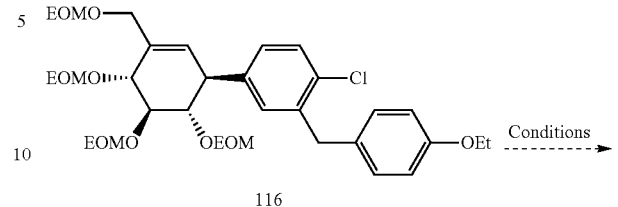

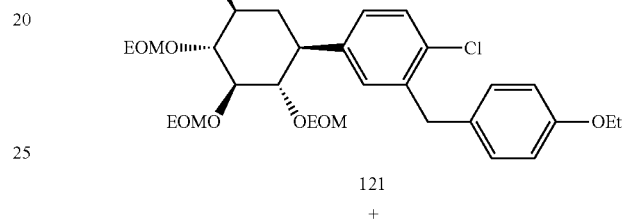

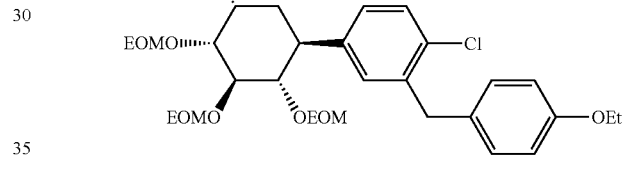

| Entry | Conditions | Results |
|---|---|---|
| 1 | H$_2$, Rh/C, MeOH, 24 h, rt | No reaction |
| 2 | H$_2$, Rh/C, EtOH, 24 h, rt | No reaction |
| 3 | H$_2$, Rh/C, iPrOH, 24 h, rt | No reaction |
| 4 | H$_2$, Rh/C, tBuOH, 24 h, rt | No reaction |
| 5 | H$_2$, Rh/C, 1,4-dioxane, 24 h, rt | No reaction |
| 6 | H$_2$, Ru/C, MeOH, 24 h, rt | No reaction |
| 7 | H$_2$, Ru/C, EtOH, 24 h, rt | No reaction |
| 8 | H$_2$, Ru/C, iPrOH, 24 h, rt | No reaction |
| 9 | H$_2$, Ru/C, tBuOH, 24 h, rt | No reaction |
| 10 | H$_2$, Ru/C, 1,4-dioxane, 24 h, rt | No reaction |

TABLE 10

Diimide reductions on 116

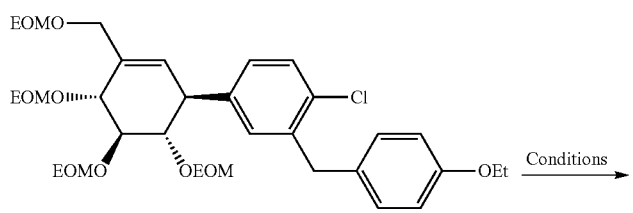

TABLE 10-continued

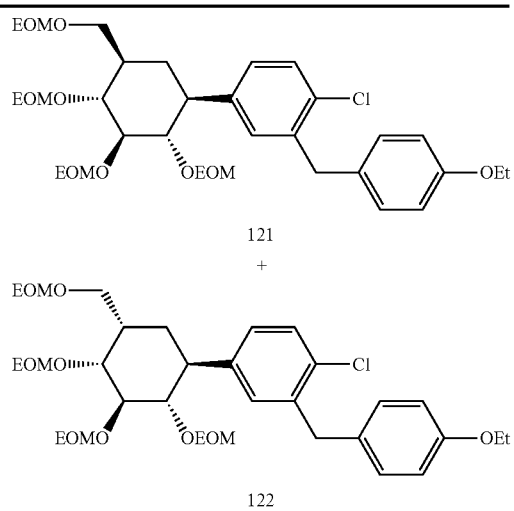

| Entry | Conditions | Results |
|---|---|---|
| 1 | pTsNHNH$_2$, NaOAc, THF/H$_2$O (1:1), 70° C., 5 d, (Reagent added every 4 h) | 121 + 122, 82% |
| 2 | pTsNHNH$_2$, NaOAc, THF/H$_2$O (1:1), 90° C., 10 d, (Reagent added every 4 h) | 121 + 122, 85% |
| 3 | pTsNHNH$_2$, NaOAc, THF/H$_2$O (1:1), 50° C., 7 d, (Reagent added every 4 h) | No Reaction |
| 4 | pTsNHNH$_2$, NaOAc, THF, 70° C., 7 d, (Reagent added every 4 h) | 121 + 122, 74% |
| 5 | pTsNHNH$_2$, NaOAc, THF/H$_2$O (1:1), 70° C., 4.5 h, (Reagent added every 5 min) | 121 + 122, 83% |

TABLE 11

NMR analysis of tetraol 80

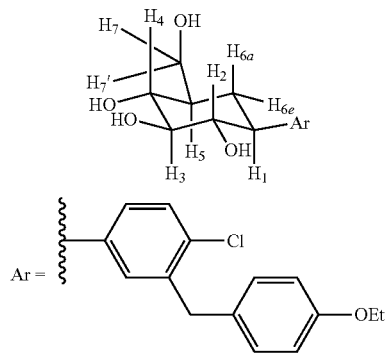

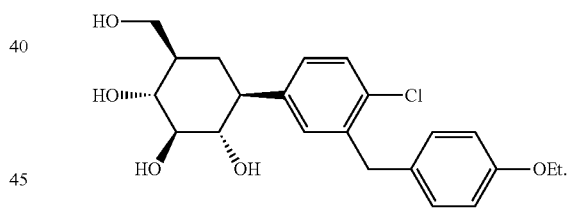

| Proton | Splitting Pattern and Coupling Constant | Chemical Shift |
|---|---|---|
| H$_{6a}$ | q, J = 13 Hz | 1.39 ppm |
| H$_5$ | m | 1.62-1.67 ppm |
| H$_{6e}$ | dt, J = 13.7, 3.4 Hz | 1.80 ppm |
| H$_1$ | ddd, J = 3.4, 10.6, 12.7 Hz | 2.56 ppm |
| H$_3$ and H$_4$ | Overlapped | 3.29-3.32 ppm |
| H$_2$ | dd, J = 9.0, 10.2 Hz | 3.44 ppm |
| H$_7$/H$_{7'}$ | dd, J = 3.7, 10.8 Hz | 3.75 ppm |

What is claimed is:

1. An aryl pseudo-C-glycoside compound having the structure of:

2. A pharmaceutical composition comprising the compound of claim 1 and a pharmaceutically acceptable excipient.

3. A method for modulating sugar metabolism, comprising the step of administering to a patient in need thereof an effective amount of the compound of claim 1.

4. The method of claim 3, wherein the patient has been diagnosed with diabetes.

5. The method of claim 3, wherein the patient has been diagnosed with metabolic syndrome.

6. The method of claim 3, wherein the patient has not been diagnosed with diabetes or metabolic syndrome but is at risk of developing diabetes or metabolic syndrome.

7. The method of claim 3, wherein the compound is administered to the subject by oral ingestion, topical application, or injection.

8. The method of claim 7, wherein the injection is subcutaneous, intravenous, intramuscular, or intraperitoneal injection.

* * * * *

UNITED STATES PATENT AND TRADEMARK OFFICE
CERTIFICATE OF CORRECTION

PATENT NO. : 10,759,729 B2  
APPLICATION NO. : 15/345252  
DATED : September 1, 2020  
INVENTOR(S) : Tony Kung Ming Shing et al.

Page 1 of 1

It is certified that error appears in the above-identified patent and that said Letters Patent is hereby corrected as shown below:

In the Claims

In Claim 1, Column 58, Lines 39-45, please delete the following compound:

"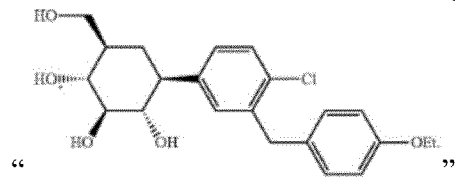"

And replace with the following compound:

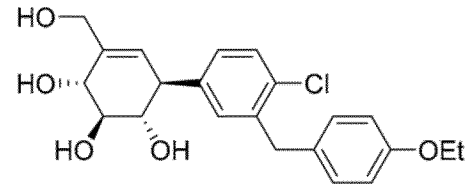

Signed and Sealed this  
Thirty-first Day of May, 2022

Katherine Kelly Vidal  
*Director of the United States Patent and Trademark Office*